(12) United States Patent
Fyfe et al.

(10) Patent No.: US 7,622,115 B2
(45) Date of Patent: Nov. 24, 2009

(54) TREATMENT WITH ANTI-VEGF ANTIBODIES

(75) Inventors: Gwendolyn Fyfe, San Francisco, CA (US); Eric Holmgren, Palo Alto, CA (US); Robert D. Mass, Mill Valley, CA (US); William Novotny, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/763,263

(22) Filed: Jun. 14, 2007

(65) Prior Publication Data

US 2007/0258984 A1 Nov. 8, 2007

Related U.S. Application Data

(63) Continuation of application No. 10/857,249, filed on May 28, 2004, now abandoned.

(60) Provisional application No. 60/474,480, filed on May 30, 2003.

(51) Int. Cl.
*A61K 39/395* (2006.01)
(52) U.S. Cl. .............. 424/143.1; 424/141.1; 424/155.1
(58) Field of Classification Search .................. None
See application file for complete search history.

(56) References Cited

U.S. PATENT DOCUMENTS

| | | | |
|---|---|---|---|
| 5,036,003 A | 7/1991 | Olander et al. |
| 6,416,758 B1 | 7/2002 | Thorpe et al. |
| 6,582,959 B2 | 6/2003 | Kim |
| 6,884,879 B1 | 4/2005 | Baca et al. |
| 7,060,269 B1 | 6/2006 | Baca et al. |
| 7,169,901 B2 | 1/2007 | Baca et al. |
| 7,227,004 B2 | 6/2007 | Kim |
| 7,297,334 B2 | 11/2007 | Baca et al. |
| 7,365,166 B2 | 4/2008 | Baca et al. |
| 7,375,193 B2 | 5/2008 | Baca et al. |
| 7,482,005 B2 | 1/2009 | Kim |
| 2002/0032315 A1 | 3/2002 | Baca et al. |
| 2002/0098187 A1 | 7/2002 | Ferrara et al. |
| 2003/0023046 A1 | 1/2003 | Ferrara et al. |
| 2004/0122018 A1 | 6/2004 | Zhu et al. |
| 2005/0053599 A1 | 3/2005 | Van Bruggen et al. |
| 2005/0186208 A1 | 8/2005 | Fyfe et al. |
| 2005/0244405 A1 | 11/2005 | Van Bruggen et al. |
| 2006/0193862 A1 | 8/2006 | Ferrara et al. |
| 2007/0025999 A1 | 2/2007 | Fyfe et al. |
| 2007/0031413 A1 | 2/2007 | Fyfe et al. |
| 2007/0036753 A1 | 2/2007 | Fyfe et al. |
| 2007/0036754 A1 | 2/2007 | Fyfe et al. |
| 2007/0036755 A1 | 2/2007 | Fyfe et al. |
| 2007/0036790 A1 | 2/2007 | Fyfe et al. |
| 2007/0059302 A1 | 3/2007 | Baca et al. |
| 2007/0071718 A1 | 3/2007 | Fyfe et al. |
| 2007/0071748 A1 | 3/2007 | Fyfe et al. |
| 2007/0071749 A1 | 3/2007 | Fyfe et al. |
| 2007/0110755 A1 | 5/2007 | Ferrara et al. |
| 2007/0148177 A1 | 6/2007 | Fyfe et al. |
| 2007/0148178 A1 | 6/2007 | Fyfe et al. |
| 2007/0154483 A1 | 7/2007 | Fyfe et al. |
| 2007/0160608 A1 | 7/2007 | Fyfe et al. |
| 2007/0196374 A1 | 8/2007 | Baca et al. |
| 2007/0253959 A1 | 11/2007 | Ferrara et al. |
| 2007/0258980 A1 | 11/2007 | Van Bruggen et al. |
| 2008/0160029 A1 | 7/2008 | Fyfe et al. |
| 2008/0166351 A1 | 7/2008 | Fyfe et al. |
| 2008/0181900 A1 | 7/2008 | Ferrara et al. |
| 2008/0187534 A1 | 8/2008 | Baca et al. |
| 2008/0226629 A1 | 9/2008 | Baca et al. |
| 2008/0241148 A1 | 10/2008 | Fyfe et al. |
| 2008/0248036 A1 | 10/2008 | Fyfe et al. |
| 2008/0248049 A1 | 10/2008 | Fyfe et al. |
| 2008/0267968 A1 | 10/2008 | Fyfe et al. |
| 2008/0279860 A1 | 11/2008 | Fyfe et al. |
| 2008/0292630 A1 | 11/2008 | Fyfe et al. |
| 2008/0292631 A1 | 11/2008 | Fyfe et al. |
| 2008/0299116 A1 | 12/2008 | Van Bruggen et al. |
| 2008/0311118 A1 | 12/2008 | Van Bruggen et al. |
| 2009/0010881 A1 | 1/2009 | Fyfe et al. |
| 2009/0010883 A1 | 1/2009 | Fyfe et al. |
| 2009/0053216 A1 | 2/2009 | Fyfe et al. |
| 2009/0081232 A1 | 3/2009 | Kim |

FOREIGN PATENT DOCUMENTS

| | | |
|---|---|---|
| CN | 1445242 A | 10/2003 |
| EP | 0 666 868 B1 | 4/2002 |
| JP | 10114680 A | 6/1998 |
| RU | 2 177 349 | 12/2001 |
| RU | 2177349 | 12/2001 |
| WO | WO 92/14748 | 3/1992 |
| WO | 98/45331 | 10/1998 |
| WO | WO 98/45331 | 10/1998 |
| WO | WO 98/45332 | 10/1998 |
| WO | WO 2007/107329 | 9/2007 |

OTHER PUBLICATIONS

Gordon et al (J of Clinical Oncology, Feb. 2001, 19:843-850, IDS).*
US News & World Report.com, Dec. 10, 2008, 2 pages.*
Braun et al., "New Systemic Frontline Treatment for Metastatic Colorectal Carcinoma" *Cancer* 100:1558-1577 (2004).
D'Orazio et al., "Adding a Humanized Antibody to Vascular Endothelial Growth Factor (Bevacizumab, Avastin™) to Chemotherapy Improves Survival in Metastatic Colorectal Cancer" *Clinical Colorectal Cancer* 3:85-88 (2003).

(Continued)

*Primary Examiner*—Laura B Goddard

(57) ABSTRACT

This invention concerns in general treatment of diseases and pathological conditions with anti-VEGF antibodies. More specifically, the invention concerns the treatment of human patients susceptible to or diagnosed with cancer using an anti-VEGF antibody, preferably in combination with one or more additional anti-tumor therapeutic agents.

5 Claims, 5 Drawing Sheets

OTHER PUBLICATIONS de Gramont et al., "Leucovorin and Fluorouracil With or Without Oxaliplatin as First-Line Treatment in Advanced Colorectal Cancer" *Journal of Clinical Oncology* 18:2938-2947 (2000).

Douillard et al., "Irinotecan combined with fluorouracil compared with fluorouracil alone as first-line treatment for metastatic colorectal cancer: a multicentre randomised trial" *Lancet* 355:1041-1047 (2000).

Fernando and Hurwitz, "Targeted Therapy of Colorectal Cancer: Clinical Experience with Bevacizumab" *The Oncologist* 9(suppl 1):11-18 (2004).

Ferrara et al., "Discovery and Development of Bevacizumab, an Anti-VEGF Antibody for Treating Cancer" *Nature Reviews-Drug Discovery* 3:391-400 (May 2004).

Goldberg at al., "A Randomized Controlled Trial of Fluorouracil Plus Leucovorin, Irinotecan, and Oxaliplatin Combinations in Patients With Previously Untreated Metastatic Colorectal Cancer" *Journal of Clinical Oncology* 22:23-30 (2004.

Hejna et al., "Phase II study of second-line oxaliplatin, irinotecan and mitomycin C in patients with advanced or metastatic colorectal cancer" *Anti-Cancer Drugs* 11:629-34 (2000).

Hurwitz et al., "Bevacizumab (a monoclonal antibody to vascular endothelial growth factor) prolongs survival in . . ." *ASCO American Society of Clinical Oncology (www.asco.org/hurwitz__no3646)* Abstract No. 3646 (May 2003).

Hurwitz et al., "Bevacizumab plus Irinotecan, Fluorouracil, and Leucovorin for Metastatic Colorectal Cancer" *N. Engl J Med* 350(23):2335-2342 (Jun. 23, 2004).

Kabbinavar et al., "Phase II, Randomized Trial Comparing Bevacizumab Plus Fluorouracil (FU) /Leucovorin (LV) With FU/LV Alone in Patients With Metastatic Colorectal Cancer" *Journal of Clinical Oncology* 21(1):60-65 (Jan. 1, 2003).

Margolin K, et al., "Phase Ib trial of intravenous recombinant humanized monoclonal antibody to vascular endothelial growth factor in combination with chemotherapy in patients with advanced cancer: Pharmacologic and long-term safety data" *J Clin Oncol* 19:851-856 (2001).

Saltz et al., "Irinotecan Plus Fluorouracil and Leucovorin for Metastatic Colorectal Cancer" *New England J. of Medicine* 343:905-914 (2000).

Yang et al., "Eradication of Established Tumors by a Fully Human Monoclonal Antibody to the Epidermal Growth Factor Receptor without Concomitant Chemotherapy" *Cancer Research* 59:1236-1243 (Mar. 15, 1999).

Folkman, Judah, "Angiogenesis in cancer, vascular, rheumatoid and other disease" *Nature Medicine* 1:27-31 (1995).

Jain, Rakesh K., "Normalization of Tumor Vasculature: An Emerging Concept in Antiangiogenic Therapy" *Science* 307:58-62 (2005).

Joo et al., "Cyclooxygenase-2 Overexpression Correlates With Vascular Endothelial Growth Factor Expression and Tumor Angiogenesis in Gastric Cancer" *J. Clin. Gastroenterol* 37:28-33 (2003).

Avastin® Product Label, May 2009.

Burstein HJ, et al., "Phase II trial of the anti-VEGF antibody bevacizumab in combination with vinorelbine for refractory advanced breast cancer" *Breast Cancer Res Treat* 76:S115 (2002).

Folkman, J, "Anti-angiogenesis Agents" *Cancer Principles & Practice of Oncology* (Chapter 63), 7th Edition edition pp. 2865-2882 (2005).

Fountzilas et al., "Paclitaxel and Carboplatin as First-Line Chemotherapy for Advanced Breast Cancer" *Oncology* (Supplement No. 1) pp. 45-48 (Jan. 1998).

Friedman et al, "Irinotecan Therapy in Adults With Recurrent or Progressive Malignant Glioma" *Journal of Clinical Oncology* 17(5):1516-1525 (May 1999).

Giles et al., "Phase II Study of Troxacitabine, a Novel Dioxolane Nucleoside Analog, in Patients With Refractory Leukemia" *Journal of Clinical Oncology* 20(3):656-664 (Feb. 1, 2002).

Gossmann et al, "Dynamic Contrast-Enhanced Magnetic Resonance Imaging as a Surrogate Marker of Tumor Response to Anti-Angiogenic Therapy in a Xenograft Model of Glioblastoma Multiforme" *J. of Magnetic Resonance Imaging* 15:233-240 (2002).

Herbst at al., "Epidermal growth factor receptors as a target for cancer treatment: the emerging role of IMC-C225 in the treatment of lung and head and neck cancers" *Semin Oncol.* 29 (1 Suppl 4):27-36 (Feb. 2002).

Herbst, "Targeted Therapy in Non-Small-Cell Lung Cancer" *Oncology* 16(9, Supplement):19-24 (Sep. 2002).

Miller, Kathy D., "E2100: A Phase III Trial of Paclitaxel Versus Paclitaxel/Bevacizumab for Metastatic Breast Cancer" *Clinical Breast Cancer* 3 (6):421-422 (Feb. 2003).

Office Action mailed Apr. 10, 2006 in U.S. Appl. No. 10/461,852.
Office Action mailed Apr. 14, 1998 in U.S. Appl. No. 08/950,863.
Office Action mailed Apr. 14, 1999 in U.S. Appl. No. 08/908,469.
Office Action mailed Apr. 14, 2000 in U.S. Appl. No. 08/950,863.
Office Action mailed Apr. 14, 2000 in U.S. Appl. No. 09/056,161.
Office Action mailed Apr. 15, 1997 in U.S. Appl. No. 08/711,314.
Office Action mailed Apr. 16, 2009 in U.S. Appl. No. 11/763,288.
Office Action mailed Apr. 2, 2002 in U.S. Appl. No. 09/723,727.
Office Action mailed Apr. 26, 1993 in U.S. Appl. No. 07/968,028.
Office Action mailed Apr. 26, 2005 in U.S. Appl. No. 10/234,671.
Office Action mailed Apr. 3, 2009 in U.S. Appl. No. 12/401,179.
Office Action mailed Apr. 7, 2000 in U.S. Appl. No. 08/839,420.
Office Action mailed Apr. 8, 2002 in U.S. Appl. No. 08/950,863.
Office Action mailed Apr. 9, 2003 in U.S. Appl. No. 09/218,481.
Office Action mailed Aug. 1, 1997 in U.S. Appl. No. 08/772,742.
Office Action mailed Aug. 11, 2000 in U.S. Appl. No. 08/908,469.
Office Action mailed Aug. 17, 2006 in U.S. Appl. No. 10/104,427.
Office Action mailed Aug. 2, 1996 in U.S. Appl. No. 08/413,305.
Office Action mailed Aug. 2, 2001 in U.S. Appl. No. 08/772,742.
Office Action mailed Aug. 3, 2001 in U.S. Appl. No. 09/056,160.
Office Action mailed Aug. 31, 1998 in U.S. Appl. No. 08/908,469.
Office Action mailed Aug. 31, 2007 in U.S. Appl. No. 11/536,603.
Office Action mailed Dec. 1, 2008 in U.S. Appl. No. 11/536,881.
Office Action mailed Dec. 10, 1998 in U.S. Appl. No. 08/950,863.
Office Action mailed Dec. 13, 2002 in U.S. Appl. No. 10/246,875.
Office Action mailed Dec. 13, 2007 in U.S. Appl. No. 11/536,931.
Office Action mailed Dec. 13, 2007 in U.S. Appl. No. 11/537,310.
Office Action mailed Dec. 14, 2006 in U.S. Appl. No. 10/857,249.
Office Action mailed Dec. 2, 1992 in U.S. Appl. No. 07/677,215.
Office Action mailed Dec. 20, 2006 in U.S. Appl. No. 11/418,774.
Office Action mailed Dec. 28, 2007 in U.S. Appl. No. 11/537,313.
Office Action mailed Dec. 29, 2008 in U.S. Appl. No. 11/536,871.
Office Action mailed Dec. 3, 1999 in U.S. Appl. No. 08/772,742.
Office Action mailed Dec. 9, 1996 in U.S. Appl. No. 08/642,554.
Office Action mailed Feb. 18, 1998 in U.S. Appl. No. 08/772,742.
Office Action mailed Feb. 18, 1998 in U.S. Appl. No. 08/970,591.
Office Action mailed Feb. 2, 2006 in U.S. Appl. No. 10/234,671.
Office Action mailed Feb. 22, 2001 in U.S. Appl. No. 08/970,591.
Office Action mailed Feb. 23, 2009 in U.S. Appl. No. 12/329,428.
Office Action mailed Feb. 26, 2003 in U.S. Appl. No. 09/718,694.
Office Action mailed Feb. 3, 2005 in U.S. Appl. No. 10/104,427.
Office Action mailed Feb. 6, 2008 in U.S. Appl. No. 11/537,542.
Office Action mailed Jan. 14, 2008 in U.S. Appl. No. 11/537,553.
Office Action mailed Jan. 15, 1999 in U.S. Appl. No. 08/839,420.
Office Action mailed Jan. 15, 2008 in U.S. Appl. No. 11/537,520.
Office Action mailed Jan. 17, 2003 in U.S. Appl. No. 09/723,752.
Office Action mailed Jan. 19, 2000 in U.S. Appl. No. 08/970,591.
Office Action mailed Jan. 2, 2001 in U.S. Appl. No. 09/056,161.
Office Action mailed Jan. 23, 2002 in U.S. Appl. No. 09/723,728.
Office Action mailed Jan. 24, 2001 in U.S. Appl. No. 09/056,160.
Office Action mailed Jan. 25, 1994 in U.S. Appl. No. 08/143,908.
Office Action mailed Jan. 26, 2005 in U.S. Appl. No. 10/441,728.
Office Action mailed Jan. 29, 2008 in U.S. Appl. No. 11/536,881.
Office Action mailed Jan. 29, 2008 in U.S. Appl. No. 11/536,908.
Office Action mailed Jan. 29, 2008 in U.S. Appl. No. 11/537,527.
Office Action mailed Jan. 31, 2006 in U.S. Appl. No. 10/441,728.
Office Action mailed Jul. 11, 2006 in U.S. Appl. No. 10/683,043.
Office Action mailed Jul. 27, 1993 in U.S. Appl. No. 08/071,214.
Office Action mailed Jul. 3, 2000 in U.S. Appl. No. 08/772,742.
Office Action mailed Jul. 9, 2002 in U.S. Appl. No. 08/908,469.
Office Action mailed Jun. 11, 2009 in U.S. Appl. No. 11/537,453.
Office Action mailed Jun. 21, 1996 in U.S. Appl. No. 08/459,206.
Office Action mailed Jun. 23, 1998 in U.S. Appl. No. 08/839,420.
Office Action mailed Jun. 25, 2002 in U.S. Appl. No. 09/218,481.

Office Action mailed Jun. 28, 2006 in U.S. Appl. No. 10/648,816.
Office Action mailed Jun. 4, 2002 in U.S. Appl. No. 09/718,694.
Office Action mailed Jun. 5, 2000 in U.S. Appl. No. 09/218,481.
Office Action mailed Mar. 10, 1992 in U.S. Appl. No. 07/677,215.
Office Action mailed Mar. 11, 2005 in U.S. Appl. No. 10/461,852.
Office Action mailed Mar. 12, 2007 in U.S. Appl. No. 10/683,043.
Office Action mailed Mar. 14, 2007 in U.S. Appl. No. 10/648,816.
Office Action mailed Mar. 17, 2004 in U.S. Appl. No. 10/441,728.
Office Action mailed Mar. 18, 2002 in U.S. Appl. No. 08/772,742.
Office Action mailed Mar. 26, 2002 in U.S. Appl. No. 09/723,726.
Office Action mailed Mar. 27, 1995 in U.S. Appl. No. 08/378,912.
Office Action mailed Mar. 28, 2008 in U.S. Appl. No. 11/537,560.
Office Action mailed Mar. 29, 1994 in U.S. Appl. No. 08/185,291.
Office Action mailed Mar. 4, 1996 in U.S. Appl. No. 08/558,042.
Office Action mailed Mar. 9, 2001 in U.S. Appl. No. 09/218,481.
Office Action mailed May 14, 1997 in U.S. Appl. No. 08/792,079.
Office Action mailed May 15, 1995 in U.S. Appl. No. 08/416,543.
Office Action mailed May 17, 2001 in U.S. Appl. No. 08/839,420.
Office Action mailed May 18, 1999 in U.S. Appl. No. 08/772,742.
Office Action mailed May 21, 1999 in U.S. Appl. No. 08/970,591.
Office Action mailed May 22, 2000 in U.S. Appl. No. 09/056,160.
Office Action mailed May 28, 2009 in U.S. Appl. No. 11/536,785.
Office Action mailed May 28, 2009 in U.S. Appl. No. 12/180,249.
Office Action mailed May 29, 2009 in U.S. Appl. No. 12/127,733.
Office Action mailed May 29, 2009 in U.S. Appl. No. 12/138,611.
Office Action mailed May 29, 2009 in U.S. Appl. No. 12/139,186.
Office Action mailed May 29, 2009 in U.S. Appl. No. 12/173,764.
Office Action mailed May 30, 2001 in U.S. Appl. No. 08/950,863.
Office Action mailed Nov. 18, 1997 in U.S. Appl. No. 08/833,504.
Office Action mailed Nov. 26, 2001 in U.S. Appl. No. 09/218,481.
Office Action mailed Nov. 29, 2007 in U.S. Appl. No. 11/536,947.
Office Action mailed Nov. 30, 2007 in U.S. Appl. No. 11/537,281.
Office Action mailed Nov. 8, 2001 in U.S. Appl. No. 08/908,469.
Office Action mailed Nov. 8, 2007 in U.S. Appl. No. 11/537,015.
Office Action mailed Oct. 1, 2008 in U.S. Appl. No. 11/935,897.
Office Action mailed Oct. 12, 1999 in U.S. Appl. No. 08/950,863.
Office Action mailed Oct. 17, 2006 in U.S. Appl. No. 10/974,591.
Office Action mailed Oct. 19, 2007 in U.S. Appl. No. 10/683,043.
Office Action mailed Oct. 25, 2007 in U.S. Appl. No. 10/648,816.
Office Action mailed Oct. 28, 2003 in U.S. Appl. No. 08/908,469.
Office Action mailed Oct. 3, 2007 in U.S. Appl. No. 11/560,524.
Office Action mailed Sep. 1, 1998 in U.S. Appl. No. 08/772,742.
Office Action mailed Sep. 1, 1998 in U.S. Appl. No. 08/970,591.
Office Action mailed Sep. 10, 2008 in U.S. Appl. No. 12/052,524.
Office Action mailed Sep. 20, 2007 in U.S. Appl. No. 11/766,051.
Office Action mailed Sep. 25, 2007 in U.S. Appl. No. 10/104,427.
Office Action mailed Sep. 26, 2003 in U.S. Appl. No. 09/723,752.
Office Action mailed Sep. 29, 1999 in U.S. Appl. No. 08/839,420.
Stopeck et al, "Results of a Phase 1 Dose-escalating Study of the Antiangiogenic Agent, SU5416, in Patients with Advanced Malignancies" *Clinical Cancer Research* 8 :2798-2805 (Sep. 2002).
Kindler et al., "Metastatic colorectal cancer" *Curr Treat Options Oncol* 2(6):459-71 (Dec 2001).
Ministry of Health of The Russian Federation, "On Standards (Protocols) For The Diagnosis and Treatment of Patients With Diseases of The Digestive Organs" Order No. 125 (Apr. 17, 1998).
Ministry of Health of The Russian Federation, "On Standards (Protocols) For The Diagnosis and Treatment of Patients With Diseases of The Digestive Organs" Order No. 125: (English Translation) (Apr. 17, 1998).
Vyshkovskiy G.L., "You came in a chemist's shop. Drug, formulations, package" *RLS—Patient 2003*, Chapter 2.2, pp. 1052 (2002).
Vyshkovskiy G.L., "You came in a chemist's shop. Drug, formulations, package" *RLS—Patient 2003*, Chapter 2.2, pp. 1052 (English Translation) (2002).
"Current Clinical Trials of the Anti-VEGF Monoclonal Antibody Bevacizumab" *Oncology* 15(8) :web pp. 1-6 (Aug. 2001).
American Cancer Society web page, "What Is Small Cell Lung Cancer?" pp. 1-4, printed Jan. 11, 2008.
Crew, "Vascular Endothelial Growth Factor: An Important Angiogenic Mediator in Bladder Cancer" *European Urology* 35:2-8 (1999).

DeVore et al., "A Randomized Phase II Trial Comparing Rhumab VEGF (Recombinant Humanized-Monoclonal Antibody to Vascular Endothelial Cell Growth Factor) Plus Carboplatin/Paclitaxel (CP) to CP Alone in Patients with Stage IIIB/IV NSCLC" *Proceedings of the American Society of Clinical Oncology* Abstract No 2000 ASCO meeting.
Drugs R&D, "Bevacizumab Anti-VEGF Monoclonal Antibody, Avastin, Rhumab-VEGF" 3(1):28-30 (2002).
Fiorica et al, "Phase II Trial of Topotecan and Cisplatin in Persistent or Recurrent Squamous and Nonsquamous Carcinomas of the Cervix" *Gynecologic Oncology* 85:89-94 (2002).
Folkman and Klagsbrun, "Angiogenic factors" *Science* 235:442-447 (1987).
Fontanini et al., "A high vascular count and overexpression of vascular endothelial growth factor are associated with unfavourable prognosis in operated small cell lung carcinoma" *British Journal of Cancer* 86 :558-563 (2002).
Fujimoto et. al., "Clinical implications of expression of vascular endothelial growth factor in metastatic lesions of ovariann cancers" *British Journal of Cancer* 85(3):313-316 (2001).
Giles, Francis J., "The Vascular Endothelial Growth Factor (VEGF) Signaling Pathway: A Therapeutic Target in Patients with Hematologic Malignancies" *The Oncologist* 6(suppl 5):32-39 (2001).
Hasan et al, "VEGF Antagonists" *Expert Opin. Biol. Ther.* 1(4):703-718 (2001).
Hsei et al, "Complexation of VEGF with Bevacizumab Decreases VEGF Clearance in Rats" *Pharmaceutical Research* 19(11):1753-1756 (Nov. 2002).
Hu et. al., "Vascular Endothelial Growth Factor Immunoneutralization Plus Paclitaxel Markedly Reduces Tumor Burden and Ascites in Athymic Mouse Model of Ovarian Cancer" *American Journal of Pathology* 161(5):1917-1924 (Nov. 2002).
Karp et al., "Timed Sequential Therapy (TST) of Relapsed and Refractory Adult Acute Myelogenous Leukemia (AML) with the Anti-Vascular Endothelial Growth Factor (VEGF) Monoclonal Antibody Bevacizumab" *Blood* 100(198a) :abstract 744 (Nov. 2002).
Konig et al., "Expression of vascular endothelial growth factor in diffuse malignant pleural mesothelioma" *Virchows Arch* 435:8-12 (1999).
Krystal et al., "Indolinone Tyrosine Kinase Inhibitors Block Kit Activation and Growth of Small Cell Lung Cancer Cells" *Cancer Research* 61:3660-3668 (May 1, 2001).
Loehrer et al., "Cisplatin Plus Etoposide With and Without Ifosfamide in Extensive Small-Cell Lung Cancer: A Hoosier Oncology Group Study" *J of Clinical Oncology* 13(10):2594-2599 (Oct 1995).
Marecos et al., "Antibody-Mediated versus Nontargeted Delivery in a Human Small Cell Lung Carcinoma Model" *Bioconjugate Chem.* 9:184-191 (1998).
Margolin et al, "Phase Ib Trial of Intravenous Recombinant Humanized Monoclonal Antibody to Vascular Endothelial Growth Factor in Combination With Chemotherapy in Patients With Advanced Cancer: Pharmacologic and Long-Term Safety Data" *Journal of Clinical Oncology* 19(3):851-856 (Feb. 1, 2001).
McDoniels-Silvers et al., "Differential Expression of Critical Cellular Genes in Human Lung Adenocarcinomas and Squamous Cell Carcinomas in Comparison to Normal Lung Tissues" *Neoplasia* 4(2):141-150 (2002).
Mendel et al., "Development of SU5416, a selective small molecule inhibitor of VEGF receptor tyrosine kinase activity, as an anti-angiogenesis agent" *Anti-Cancer Drug Design* 15:29-41 (2000).
Moore et al., "Gemcitabine Plus Cisplatin, an Active Regimen in Advanced Urothelial Cancer: A Phase II Trial of the National Cancer Institute of Canada Clinical Trials Group" *J of Clinical Oncology* 17(9):2876-2881 (Sep. 1999).
Multani et al., "Non-Hodgkin's Lymphoma: Review of Conventional Treatments" *Current Pharmaceutical Biotechnology* 2:279-291 (2001).
Muss, "Interferon Therapy of Metastatic Renal Cell Cancer" *Seminars in Surgical Oncology* 4:199-203 (1988).
Nowak, A. K., et al., "New Approaches for Mesothelioma: Biologics, Vaccines, Gene Therapy, and Other Novel Agents" *Seminars in Oncology* 29(1):82-96 (Feb. 2002).

O'Toole et al., "Treatment of Carcinoid Syndrome. A Prospective Crossover Evaluation of Lanreotide Versus Octreotide in Terms of Efficacy, Patient Acceptability, and Tolerance" *Cancer* 88(4):770-776 (Feb. 15, 2000).

O-charoenrat, et al, "Expression of Vascular Endothelial Growth Factor Family Members in Head and Neck Squamous Cell Carcinoma Correlates with Lymph Node Metastasis" *Cancer* 92(3):556-568 (Aug. 1, 2001).

Ohta et al., "VEGF and VEGF type C play an important role in angiogenesis and lymphangiogenesis in human malignant mesothelioma tumours" *British Journal of Cancer* 81(1):54-61 (1999).

Ohtani, et. al., "A Case of Rapidly Growing Ovarian Squamous Cell Carcinoma Successfully Controlled by Weekly Paclitaxel-Carboplatin Administration" *Gynecologic Oncology* 79:515-518 (2000).

Presta et al., "Humanization of an Anti-Vascular Endothelial Growth Factor Monoclonal Antibody for the Therapy of Solid Tumors and Other Disorders" *Cancer Research* 57(20):4593-4599 (Oct. 15, 1997).

Schoffski et al, "Docetaxel and cisplatin: An active regimen in patients with locally advanced, recurrent or metastatic squamous cell carcinoma of head and neck" *Annals of Oncology* 10:119-122 (1999).

Shimoyama et al., "Phase 1 study of TSU-16 in Japanese patients with advanced cancer. None dose-limiting headache like that in the U.S. study was observed up to 250/mg/m2" *Proc Am Soc Clin Oncol* 21:Abract No. 444 (2002).

Sirotnak et al., "Efficacy of Cytotoxic Agents against Human Tumor Xenografts Is Markedly Enhanced By Coadministration of ZD1839 (Iressa), an Inhibitor of EGFR Tyrosine Kinase" *Clinical Cancer Research* 6:4885-4892 (Dec. 2000).

Socinski et al., "Chemotherapeutic Management of Stage IV Non-Small Cell Lung Cancer" *Chest* 123:226S-243S (2003).

Takita et al., "Immunohistochemical demonstration of angiogenic growth factors and EGF receptor in hepatic metastases and primary human gastric cancer" *J Nippon Med Sch* 65(5):358-366 (1998).

Thomas et al., "Antiangiogenic Therapy in Leukemia" *Acta Haematol* 106:190-207 (2001).

Ueno Hikaru, et al., "Inhibition of PDGF β Receptor Signal Transduction by Coexpression of a Truncated Receptor" *Science* 252:844-848 (May 10, 1991).

Wong et al, "Paclitaxel-Induced Hypersensitivity Pneumonitis: Radiographic and CT Findings" *American Journal of Roentgenology* 176:718-720 (Mar. 2001).

Ellis et al., "Vascular Endothelial Growth Factor in Human Colon Cancer: Biology and Therapeutic Implications" *The Oncologist* 5(Suppl 1):11-15 (2000).

Shaheen et al., "Inhibited growth of colon cancer carcinomatosis by antibodies to vascular endothelial and epidermal growth factor receptors" *British Journal of Cancer* 85(4):584-589 (2001).

Achen et al., "Localization of Vascular Endothelial Growth Factor-D in Malignant Melanoma Suggests a Role in Tumour Angiogenesis" *Journal of Pathology* 193 :147-154 (2001).

Akagi et al., "Induction of Neuropilin-1 and Vascular Endothelial Growth Factor by Epidermal Growth Factor in Human Gastric Cancer Cells" *British Journal of Cancer* 88 : 796-802 (2003).

Aldridge et al., "Vascular Endothelial Growth Factor acts as an Osteolytic Factor in Breast Cancer Metastases to Bone" *British Journal of Cancer* 92(8):1531-1537 (2005).

Algire et al., "Vascular Reactions of Normal and Malignant Tissues in Vivo. I. Vascular Reactions of Mice to Wounds and to Normal and Neoplastic Transplants" *Journal of the National Cancer Institute* VI : 73-82 (Aug. 1945).

Aoki et al., "Expression of Cyclooxygenase-2 and Vascular Endothelial Growth Factor in Pancreatic Tumors" *Oncology Reports* 9:761-765 (2002).

Aotake et al., "Changes of Angiogenesis and Tumor Cell Apoptosis during Colorectal Carcinogenesis" *Clinical Cancer Research* 5 :135-142 (Jan. 1999).

Arteaga et al., "Epidermal Growth Factor Receptor Dependence in Human Tumors: More Than Just Expression?" *The Oncologist* (supplement 4) 7:31-39 (2002).

Autiero et al., "Role of P1GF in the intra- and intermolecular Cross Talk Between the VEGF Receptors F1t1 and F1kl" *Nature Medicine* 9(7):936-943 (Jul. 2003).

Baird et al., "Immunoreactive Fibroblast Growth Factor (FGF) in a Transplantable Chondrosarcoma: Inhibition of Tumor Growth by Antibodies to FGF" *J. Cell. Biochem.* 30:79-85 (1986).

Baluk et al., "Cellular Abnormalities of Blood Vessels as Targets in Cancer" *Current Opinion in Genetics & Development* 15:102-111 (2005).

Barbera-Guillem et al., "Vascular Endothelial Growth Factor Secretion by Tumor-infiltrating Macrophages Essentially Supports Tumor Angiogenesis, and IgG Immune Complexes Potentiate the Process" *Cancer Research* 62:7042-7049 (Dec. 1, 2002).

Barinaga, M., "Designing Therapies That Target Tumor Blood Vessel" *Science* 275:482-484 (1997).

Ben-Efraim, "Cancer Immunotherapy: Hopes and Pitfalls: A Review" *Anticancer Research* 16:3235-3240 (1996).

Benson et al., "Bevacizumab (anti-VEGF) plus FOLFOX4 in previously treated advanced colorectal cancer (advCRC): an interim toxicity analysis of the Eastern Cooperative Oncology Group (ECOG) study E3200" *Proceedings of the American Society of Clinical Oncology* 22(243):975 (2003).

Bergers et al., "Tumorigenesis and the Angiogenic Switch" *Nature* 3:401-410 (Jun. 2003).

Bouvet et al., "Adenovirus-mediated Wild-Type p53 Gene Transfer Down-Regulates Vascular Endothelial Growth Factor Expression and Inhibits Angiogenesis in Human Colon Cancer" *Cancer Research* 58:2288-2292 (Jun. 1, 1998).

Bremnes et al., "Angiogenesis in non-small cell lung cancer: The prognostic impact of neoangiogenesis and the cytokines VEGF and bFGF in tumours and blood" *Lung Cancer* 51:143-158 (2006).

Brown et al., "Expression of vascular permeability factor (vascular endothelial growth factor) and its receptors in breast cancer" *Human Pathology* 26(1):86-91 (1995).

Buchler et al., "VEGF-RII Influences the Prognosis of Pancreatic Cancer" *Annals of Surgery* 236(6):738-749, 2002.

Burstein HJ, et al., "Phase II trial of the anti-VEGF antibody bevacizumab in combination with vinorelbine for refractory advanced breast cancer." *Breast Cancer Res Treat* 76:S115 (2002).

Burstein HJ, et al., "Phase II trial of the anti-VEGF antibody bevacizumab in combination with vinorelbine for refractory advanced breast cancer" *25th Annual San Antonio Breast Cancer Symposium*, (2002).

Buteau-Lozano et al., "Transcriptional Regulation of Vascular Endothelial Growth Factor by Estradiol and Tamoxifen in Breast Cancer Cells: A Complex Interplay between Estrogen Receptors α and β1" *Cancer Research* 62:4977-2984 (Sep. 1, 2002).

Cao et al., "Angiogenesis Stimulated by PDGF-CC, A Novel Member in the PDGFR-αα and αβ Receptors" *The FASEB Journal* 16:1575-1583 (Oct. 2002).

Carmeliet et al., "Abnormal blood vessel development and lethality in embryos lacking a single VEGF allele" *Nature* 380(6573):435-438 (Apr. 4, 1996).

Carson WE, et al., "A phase 2 trial of a recombinant humanized monoclonal anti-vascular endothelial growth factor (VEGF) antibody in patients with malignant melanoma" *Proc Am Soc Clin Oncol* 22:705 (2003).

Chen et al., "Bevacizumab (BV) plus 5-FU/leucovorin (FU/LV) for advanced colorectal cancer (CRC) that progressed after standard chemotherapies: An NCI Treatment Referral Center trial (TRC-0301)" *American Society of Clinical Oncology Meeting Proceedings* (Abstract #3515) 23 (2004).

Chen, H., "Expanding the Clinical Development of Bevacizumab" *The Oncologist* 9(suppl 1):27-35 (2004).

Ciardiello et al., "Antiangiogenic and Antitumor Activity of Anti-Epidermal Growth Factor Receptor C225 Monoclonal Antibody in Combination with Vascular Endothelial Growth Factor Antisense Oligonucleotide in Human GEO Colon Cancer Cells" *Clin Cancer Res* 6:3739-3747 (Sep. 2000).

Cilley et al., "Bevacizumab in the treatment of colorectal cancer" *Expert Opin. Biol. Ther.* 7(5):739-749 (2007).

Cobleigh MA, et al., "A Phase I/II dose-escalation trial of bevacizumab in previously treated metastatic breast cancer" *Semin Oncol* 30(suppl 16):117-124 (2003).

Connolly et al., "Human Vascular Permeability Factor" *Journal of Biological Chemistry* 264(33):20017-20024 (1989).

Costa et al., "Cyclo-Oxygenase 2 Expression is Associated with Angiogenesis and Lymph Node Metastasis in Human Breast Cancer" *Journal of Clinical Pathology* 55:429-434 (2002).

Crane CH, et al., "Preliminary results of a phase I study of rhuMab VEGF (bevacizumab) with concurrent radiotherapy (XRT) and capecitabine (CAP)" *1st annual Gastrointestinal Cancers Symposium* (San Francisco, California) (Jan. 22, 2004).

Crane CH, et al., "Preliminary results of a phase I study of rhumba VEGF (bevacizumab) with concurrent radiotherapy (XRT) and capecitabine (CAP) in locally advanced pancreatic cancer" *Eur J Cancer Suppl* 1:S294 (2003).

D'Adamo DR, et al., "Cardiac toxicity in a phase II study of doxorubicin (DOX) and bevacizumab (BEV) for patients (pts) with metastatic soft-tissue sarcomas (STS)" *Proc Am Soc Clin Oncol* 23:817 (2004).

de Vries et al., "The fms-like tyrosine kinase, a receptor for vascular endothelial growth factor" *Science* 255:989-991 (1992).

Decaussin et al., "Expression of Vascular Endothelial Growth Factor (VEGF) and Its Two Receptors (VEGF-R1-Flt1 and VEGF-R2-Flk/KDR) in Non-Small Cell Lung Carcinomas (NSCLCs): Correlation with Angiogenesis and Survival" *Journal of Pathology* 188:369-377 (1999).

Dennis and Rifkin, "Studies on the role of basic fibroblast growth factor in vivo: inability of neutralizing antibodies to block tumor growth" *J. Cellular Physiology* 144:84-98 (1990).

Des Guetz at al., "Microvessel Density and VEGF Expression are Prognostic Factors in Colorectal Cancer. Meta-analysis of the Literature" *British Journal of Cancer* 94(12):1823-1832 (2006).

Dickler M, et al., "Phase II trial of erlotinib (OSI-774), an epidermal growth factor receptor (EGFR)-tyrosine kinase inhibitor, and bevacizumab, a humanized monoclonal antibody to vascular endothelial growth factor (VEGF), in patients (pts) with metastatic breast cancer (MBC)" *Proc Am Soc*, 2004.

Dong at al., "VEGF-Null Cells Require PDGFR β Signaling-mediated Stromal Fibroblast Recruitment for Tumorigenesis" *The EMBO Journal* 23(14):2800-2810 (2004).

Dr. Napoleone Ferrara's Declaration filed in connection with European Patent Appl. No. 92923512.5 (EP Patent 0666,868B1) (Apr. 24, 1998).

Dumont et al., "Cardiovascular Failure in Mouse Embryos Deficient in VEGF Receptor-3" *Science* 282:946-949 (Oct. 30, 1998).

Dvorak et al., "Distribution of Vascular Permeability Factor (Vascular Endothelial Growth Factor) in Tumors: Concentration in Tumor Blood Vessels" *Journal of Experimental Medicine* 174:1275-1278, (1991).

Dvorak et al., "Vascular permeability factor/vascular endothelial growth factor, microvascular hyperpermeability, and angiogenesis" *American Journal of Pathology* 146(5):1029-1039 (1995).

Ebos et al., "Imatinib Mesylate (STI-571) Reduces Bcr-Abl-Mediated Vascular Endothelial Growth Factor Secretion in Chronic Myelogenous Leukemia" *Molecular Cancer Research* 1:89-95 (Dec. 2002).

Ehrmann et al., "Choriocarcinoma: Transfilter Simulation of Vasoproliferation in the Hamster Cheek Pouch—Studied by Light and Electron Microscopy" *Journal of the National Cancer Institute* 41(4):1329-1341 (Dec. 1968).

Elaraj et al., "A Pilot Study of Antiangiogenic Therapy with Bevacizumab and Thalidomide in Patients with Metastatic Renal Cell Carcinoma" *J Immunother* 27(4):259-264 (Jul. 2004).

Ellis et al., "Down-regulation of Vascular Endothelial Growth Factor in a Human Colon Carcinoma Cell Line Transfected with an Antisense Expression Vector Specific for c-src" *The Journal of Biological Chemistry* 273(2):1052-1057 (1998).

Eriksson et al., "Role of circulating cytokeratin fragments and angiogenic factors in NSCLC patients stage IIIa-IIIb receiving curatively intended treatment" *Neoplasma* 53(4):285-290 (2006).

Fehrenbacher et al., A phase II, multicenter, randomized clinical trial to evaluate the efficacy and safety of bevacizumab in combination with either chemotherapy (docetaxel or pemetrexed) or erlotinib hydrochloride compared with chemotherapy alone for treatment of recurrent or refractory non-small cell, 2006.

Ferrara and Alitalo, "Clinical applications of angiogenic growth factors and their inhibitors" *Nat Med*. 5(12):1359-1364 (Dec. 1999).

Ferrara and Henzel, "Pituitary Follicular Cells Secrete a Novel Heparin-binding Growth Factor Specific for Vascular Endothelial Cells" *Biochem. & Biophys. Res. Comm*. 161(2):851-858 (Jun. 15, 1989).

Ferrara et al., "Heterozygous embryonic lethality induced by targeted inactivation of the VEGF gene" *Nature* 380(6573):439-442 (Apr. 4, 1996).

Ferrara et al., "Molecular and biological properties of the vascular endothelial growth factor family of proteins" *Endo. Rev.* 13(1):18-32 (Feb. 1992).

Ferrara et al., "The vascular endothelial growth factor family of polypeptides" *J. Cell. Biochem*.47:211-218 (1991).

Ferrara et al., "Vascular endothelial growth factor: basic science and clinical progress" *Endocr Rev.* 25(4):581-611 (Aug. 2004).

Ferrara, "VEGF and the quest for tumour angiogenesis factors" *Nat Rev Cancer* 2(10):795-803 (Oct. 2002).

Ferrara, N., "Vascular endothelial growth factor. The trigger for neovascularization in the eye" *Laboratory Investigation* 72(6):615-618 (1995).

Ferrer et al., "Expression of Vascular Endothelial Growth Factor Receptors in Human Prostate Cancer" *Urology* 54(3):567-572 (1999).

Fleming et al., "Regulation of Vascular Endothelial Growth Factor Expression in Human Colon Carcinoma Cells by Activity of src Kinase" *Surgery* 122(2):501-507, 1997.

Foekens et al., "High Tumor Levels of Vascular Endothelial Growth Factor Predict Poor Response to Systemic Therapy in Advanced Breast Cancer" *Cancer Research* 61:5407-5414 (Jul. 15, 2001).

Folkman et al., "Induction of angiogenesis during the transition from hyperplasia to neoplasia" *Nature* 339(6219):58-61 (1989).

Folkman et al., "Isolation of a Tumor Factor Responsible for Angiogenesis" *Journal of Experimental Medicine* 133(2):275-288 (Feb. 1, 1971).

Folkman, J., "The Vascularization of Tumors" *Scientific American* 234(5):59-73 (May 1976).

Folkman, Judah M.D., "Tumor Angiogenesis:Therapeutic Implications" *New England J. of Medicine* 285(21):1182-1186 (Nov. 18, 1971).

Folkman, Judah, "Antiangiogenesis Agents" *Cancer Principles & Practice of Oncology*, 7th edition, Philadelphia:Lippincott Williams & Wilkins, Chapter 63, pp. 2565-2882.

Fontanini et al., "Angiogenesis as a Prognostic Indicator of Survival in Non-Small-Cell Lung Carcinoma: a Prospective Study" *J Natl Cancer Inst*. 89(12):881-886 (Jun. 18, 1997).

Fuckar et al., "VEGF Expression is Associated with Negative Estrogen Receptor Status in Patients with Breast Cancer" *International Journal of Surgical Pathology* 14(1):49-55 (Jan. 2006).

Fuh et al., "Structure-Function Studies of Two Synthetic Anti-vascular Endothelial Growth Factor Fabs and Comparison with the Avastin Fab" *Journal of Biological Chemistry* 281(10):6625-6631 (Mar. 10, 2006).

Fujimoto et al., "Expression of Two Angiogenic Factors, Vascular Endothelial Growth Factor and Platelet-derived Endothelial Cell Growth Factor in Human Pancreatic Cancer, and its Relationship to Angiogenesis" *Eur J Cancer* 34(9):1439-1447 (1998).

Fujisawa et al., "Effect of p53 Gene Transfection on Vascular Endothelial Growth Factor Expression in Endometrial Cancer Cells" *Experimental and Molecular Pathology* 74:276-281 (2003).

Gabrilovich et al., "Production of Vascular Endothelial Growth Factor by Human Tumors Inhibits the Functional Maturation of Dendritic Cells" *Nature Medicine* 2(10):1096-1103 (Oct. 1996).

Gaffney et al., "Epidermal Growth Factor Receptor (EGFR) and Vascular Endothelial Growth Factor (VEGF) Negatively Affect Overall Survival in Carcinoma of the Cervix" *Int. J. Radiation Oncol. Biol*. 56(4):922-928 (2003).

Gasparini et al., "Clinical Relevance of Vascular Endothelial Growth Factor and Thymidine Phosphorylase in Patients with Node-Positive Breast Cancer Treated with Either Adjuvant Chemotherapy or Hormone Therapy" *The Cancer Journal from Scientific American* 5(2) (Mar. 1999).

Gasparini et al., "Prognostic significance of vascular endothelial growth factor protein in node-negative breast carcinoma" *Journal of National Cancer Institute* 89(2):139-147 (1997).

Genentech Press Release, "Genentech Announces Second Quarter 2004 Results" (Jul. 7, 2004).

George et al., "The von Hippel-Lindau Protein, Vascular Endothelial Growth Factor, and Kidney Cancer" *N Engl J Med* 349(5):419-421 (Jul. 31, 2003).

Gerber et al., "Vascular endothelial growth factor induces expression of the antiapoptotic proteins Bc1-2 and A1 in vascular endothelial cells" *J Biol Chem.* 273(21):13313-13316 (May 22, 1998).

Gille et al., "A repressor sequence in the juxtamembrane domain of Flt-1 (VEGFR-1) constitutively inhibits vascular endothelial growth factor-dependent phosphatidylinositol 3'-kinase activation and endothelial cell migration" *EMBO Journal* 19:4064-4073 (2000).

Gimbrone, Jr. et al., "Tumor Dormancy in Vivo by Prevention of Neovascularization" *The Journal of Experimental Medicine*136:261-276 (1972).

Goldman et al., "Chronic Myeloid Leukemia—Advances in Biology and New Appoaches to Treatment" *New England J. of Medicine* 349(15):1451-1464 (Oct. 9, 2003).

Gordon MS, et al., "Phase I safety and pharmacokinetic study of recombinant human anti-vascular endothelial growth factor in patients with advanced cancer" *J Clin Oncol* 19:843-850 (2001).

Gotlib J, et al., "Phase II study of bevacizumab (anti-VEGF humanized monoclonal antibody) in patients with myelodysplastic syndrome (MDS)" *Blood* 102:425 (2003).

Greenblatt et al., "Tumor Angiogenesis: Transfilter Diffusion Studies in the Hamster by the Transparent Chamber Technique" *Journal of the National Cancer Institute* 41(1):111-124 (Jul. 1968).

Gschwind et al., "The discovery of receptor tyrosine kinases: targets for cancer therapy" *Nature* 4:361-370 (May 2004).

Guidi et al., "Association of Angiogenesis in Lymph Node Metastases with Outcome of Breast Cancer" *Journal of the National Cancer Institute* 92(6):486-492 (Mar. 15, 2000).

Guidi et al., "Vascular Permeability Factor (Vascular Endothelial Growth Factor) Expression and Angiogenesis in Patients with Ductal Carcinoma in Situ of the Breast" *American Cancer Society* 80(10):1945-1953 (Nov. 15, 1997).

Guo et al., "Overexpression of Vascular Endothelial Growth Factor by MCF-7 Breast Cancer Cells Promotes Estrogen-independent Tumor Growth in Vivo" *Cancer Research* 63:4684-4691 (Aug. 1, 2003).

Gustin DM, et al., "Phase I study of bevacizumab, fluorouracil, hydroxyurea and radiotherapy (B-FHX) for patients with poor prognosis head and neck cancer" *Proc Am Assoc Cancer Res* 44:1227 (2003).

Haase VH, "The VHL/HIF oxygen-sensing pathway and its relevance to kidney disease" *Kidney International* 69:1302-1307 (2006).

Hanahan et al., "The Hallmarks of Cancer" *Cell* 100:57-70 (Jan. 7, 2000).

Hanrahan et al., "The Angiogenic Switch for Vascular Endothelial Growth Factor (VEGF)-A, VEGF-B, VEGF-C,and VEGF-D in the Adenoma-Carcinoma Sequence During Colorectal Cancer Progression" *Journal of Pathology* 200:183-194 (2003).

Harris et al., "Therapeutic Antibodies—The Coming of Age" *TIBTECH* 11(2):42-44 (Feb. 1993).

Hedrick et al., "Post-progression therapy (PPT) effect on survival in AVF2107, a phase III trial of bevacizumab in first-line treatment of metastatic colorectal cancer (mCRC)" *American Society of Clinical Oncology Meeting Proceedings* (Abstract #3517) 23:2004 (2004).

Hellman, Samuel, "Principles of Cancer Management: Radiation Therapy", Chapter 16, pp. 265-288.

Hemmerlein et al., "Vascular endothelial growth factor expression, angiogenesis, and necrosis in renal cell carcinomas" *Virchows Arch* 439:645-652 (2001).

Herbst et al., "Angiogenesis and Lung Cancer: Prognostic and Therapeutic Implications" *Journal of Clinical Oncology* 23(14):3243-3256 (May 10, 2005).

Herbst et al., "Phase I/II Trial Evaluating the Anti-Vascular Endothelial Growth Factor Monoclonal Antibody Bevacizumab in Combination With the HER-1/Epidermal Growth Factor Receptor Tyrosine Kinase Inhibitor Erlotinib for Patients With Recurrent Non-Small-Cell Lung Cancer" *J Clin Oncol*, May 2005.

Hicklin et al., "Role of the Vascular Endothelial Growth Factor Pathway in Tumor Growth and Angiogenesis" *Journal of Clinical Oncology* 23(5):1011-1027 (Feb. 10, 2005).

Hillan KJ, et al., "The role of VEGF expression in response to Bevacizumab plus capecitabine in metastatic breast cancer (MBC)" *Proc Am Soc Clin Oncol* 22:191 (2003).

Hori et al., "Suppression of solid tumor growth by immunoneutralizing monoclonal antibody against human basic fibroblast growth factor" *Cancer Research* 51(22):6180-6184 (Nov. 15, 1991).

Huang et al., "Regulation of hypoxia-inducible factor $1\alpha$ is mediated by an $O_2$-dependent degradation domain via the ubiquitin-proteasome pathway" *Proc. Natl. Acad. Sci. USA* 95:7987-7992 (Jul. 1998).

Hyder et al., "Sex-steroid Regulation of Vascular Endothelial Growth Factor in Breast Cancer" *Endocrine-Related Cancer* 13:667-687 (2006).

Ide et al., "Vascularization of the Brown-Pearce Rabbit Epithelioma Trasnplant as Seen in the Transparent Ear Chamber" 42(6):891-899 (Dec. 1939).

Ikeda et al., "The association of K-ras gene mutation and vascular endothelial growth factor gene expression in pancreatic carcinoma" *Cancer* pp. 488-499 (Aug. 1, 2001).

Iliopoulos et al., "Negative regulation of hypoxia-inducible genes by the von Hippel-Lindau protein" *Proc. Natl. Acad. Sci. USA* 93:10595-10599 (Oct. 1996).

Imoto et al., "Vascular Endothelial Growth Factor Expression in Non-Small-Cell Lung Cancer: Prognostic Significance in Squamous Cell Carcinoma" *J Thorac Cardiovasc Surg.* 115:1007-1014 (1998).

Inai et al., "Inhibition of Vascular Endothelial Growth Factor (VEGF) Signaling in Cancer Causes Loss of Endothelial Fenestrations, Regression of Tumor Vessels, and Appearance of Basement Membrane Ghosts" *American Journal of Pathology* 165(1):35-52 (Jul. 2004).

Ishigami et al., "Predictive Value of Vascular Endothelial Growth Factor (VEGF) in Metastasis and Prognosis of Human Colorectal Cancer" *British Journal of Cancer* 78(10):1379-1384 (1998).

Itakura et al., "Enchanced Expression of Vascular Endothelial Growth Factor in Human Pancreatic Cancer Correlates with Local Disease Progression" *Clin Cancer Res* 3:1309-1316 (Aug. 1997).

Jacobs et al., "Polymorphisms in the Vascular Endothelial Growth Factor Gene and Breast Cancer in the Cancer Prevention Study II Cohort" *Breast Cancer Research* 8(2):1-6 (2006).

Jacobsen et al., "Expression of vascular endothelial growth factor protein in human renal cell carcinoma" *BJU International* 93:297-302 (2004).

Jain et al., "Normalizing Tumor Vasculature with Anti-Angiogenic Therapy: A New Paradigm for Combination Therapy" *Nature Medicine* 7(9):987-989 (Sep. 2001).

Jain et al., "Transport of Molecules Across Tumor Vasculature" *Cancer and Metastasis Reviews* 6:559-593 (1987).

Jain, R., "Barriers to drug delivery in solid tumors" *Scientific American* 271(1):58-65 (Jul. 1994).

Jain, Rakesh K., "Determinants of Tumor Blood Flow: A Reveiw" *Cancer Research* 48:2641-2658 (May 15, 1988).

Jarzynka et al., "Estradiol and nicotine exposure enhances A549 bronchioloalveolar carcinoma xenograft growth in mice through the stimulation of angiogenesis" *Int J Oncol.* 28:337-344 (2006).

Johnson DH, et al., "Randomized phase II trial comparing bevacizumab plus carboplatin and paclitaxel with carboplatin and paclitaxel alone in previously untreated locally advance or metastatic non-small cell lung cancer" *J Clin Oncol* 22:2184-2191 (2004).

Kang et al., "The Prognostic Effect of VEGF Expression in Squamous Cell Carcinoma of the Cervix Treated with Radiation Therapy Alone" *J. Korean Med. Sci.* 19:693-697 (2004).

Karp JE, et al., "Targeting vascular endothelial growth factor for relapsed and refractory adult acute myelogenous leukemias: Therapy with sequential 1-β-D-arabinofuranosylcytosine, mitoxantrone, and bevacizumab" *Clin Cancer Res* 10(11):3577-3585 (2004).

Kawai et al., "Direct Interaction between BRCA1 and the Estrogen Receptor Regulates Vascular Endothelial Growth Factor (VEGF) Transcription and Secretion in Breast Cancer Cells" *Oncogene* 21:7730-7739 (2002).

Kawasaki et al., "A Requirement for Neuropilin-1 in Embryonic Vessel Formation" *Development* 126:4895-4902 (1999).

Kaya et al., "The prognostic significance of vascular endothelial growth factor levels in sera of non-small cell lung cancer patients" *Respiratory Medicine* 98:632-636 (2004).

Keck et al., "Vascular Permeability Factor, An Endothelial Cell Mitogen Related to PDGF" *Science* 246:1309-1312 (1989).

Kim et al., "Inhibition of Vascular Endothelial Growth Factor-Induced Angiogenesis Suppresses Tumour Growth in vivo" *Nature* 362:841-844 (Apr. 29, 1993).

Kim et al., "The Vascular Endothelial Growth Factor Proteins: Identification of Biologically Relevant Regions by Neutralizing Monoclonal Antibodies" *Growth Factors* 7(1):53-64 (1992).

Kindler et al., "A double-blind, placebo-controlled, randomized phase III trial of gemcitabine (G) plus bevacizumab (B) versus gemcitabine plus placebo (P) in patients (pts) with advanced pancreatic cancer (PC): A preliminary analysis of Cancer and Leukemia Group B (CALGB) 80303." *ASCO* Abstract No. 108 (2007).

Kindler et al., "A randomized phase II study of bevacizumab (B) and gemcitabine (G) plus cetuximab (C) or erlotinib (E) in patients (pts) with advanced pancreatic cancer (PC) : A preliminary analysis" *ASCO* Abstract No. 4040 (2006).

Kindler et al., "Phase II Trial of Bevacizumab Plus Gemcitabine in Patients With Advanced Pancreatic Cancer" *J Clin Oncol* 23(31):8033-8040 (Nov. 1, 2005).

Kindler HL, et al., "Bevacizumab (B) plus gemcitabine (G) in patient (pts) with advanced pancreatic cancer" *Proc Am Soc Clin Oncol* 23:314 (2004).

Kindler HL, et al., "Bevacizumab (B) plus gemcitabine (G) in patients (pts) with advanced pancreatic cancer (PC)" *Proc Am Soc Clin Oncol* 22:259 (2003).

Kindler HL, et al., "Bevacizumab plus gemcitabine is an active combination in patients with advanced pancreatic cancer: interim results of an ongoing phase II trial from the University of Chicago phase II Consortium" *Gastrointestinal Cancers Symposium* Abstract 86 (2004).

Klagsbrun and D'Amore, "Regulators of angiogenesis" *Ann. Rev. Physiol.* 53:217-239 (1991).

Kondo et al., "Enhancement of Angiogenesis, Tumor Growth, and Metastasis by Transfection of Vascular Endothelial Growth Factor into LoVo Human Colon Cancer Cell Line" *Clinical Cancer Research* 6:622-630 (Feb. 2000).

Konecny et al., "Association Between HER-2/neu and Vascular Endothelial Growth Factor Expression Predicts Clinical Outcome in Primary Breast Cancer Patients" *Clinical Cancer Research* 10:1706-1716 (Mar. 1, 2004).

Konishi et al., "The K-ras Gene Regulates Vascular Endothelial Growth Factor Gene Expression in Non-small Cell Lung Cancers" *International Journal of Oncology* 16:501-511 (2000).

Koukourakis et al., "Vascular Endothelial Growth Factor/KDR Activated Microvessel Density versus CD31 Standard Microvessel Density in Non-Small Cell Lung Cancer" *Cancer Research* 60:3088-3095 (Jun. 1, 2000).

Kumar et al., "The Role of HER2 in Angiogenesis" *Seminars in Oncology* (Suppl. 16) 28(5):27-32 (Oct. 2001).

Kuniyasu et al., "Induction of Angiogenesis by Hyperplastic Colonic Mucosa Adjacent to Colon Cancer" *American Journal of Pathology* 157(5):1523-1535 (Nov. 2000).

Kuramochi et al., "Vascular Endothelial Growth Factor Messenger RNA Expression Level is Preserved in Liver Metastases Compared with Corresponding Primary Colorectal Cancer" *Clin. Cancer Res.* 12(1):29-33 (Jan. 1, 2006).

Kyzas et al., "Prognostic Significance of VEGF Immunohistochemical Expression and Tumor Angiogenesis in Head and Neck Squamous Cell Carcinoma" *J. Cancer Research and Clinical Oncology* 131:624-630 (2005).

Langmuir et al., "Successful long-term therapy with bevacizumab (Avastin) in solid tumors" *Proc Am Soc Clin Oncol* (Abstract #32) 21:9a (2002).

Lee et al., "Expression of Vascular Endothelial Growth Factor in Renal Cell Carcinoma and the Relation to Angiogenesis and p53 Protein Expression" *J Surg Oncol*. 77:55-60 (2001).

Leslie III et al., "Vascular Endothelial Growth Factor Receptor-1 Mediates Migration of Human Colorectal Carcinoma Cells by Activation of Src Family Kinases" *British Journal of Cancer* 94:1710-1717 (2006).

Leung et al., "Vascular Endothelial Growth Factor is a Secreted Angiogenic Mitogen" *Science* 246(4935):1306-1309 (Dec. 8, 1989).

Lewis, Warren H., "The Vascular Patterns of Tumors" *Bulletin of The Johns Hopkins Hospital* XLI:156-162 (1927).

Li et al., "Monoclonal Antibodies to Recombinant Human Vascular Endothelial Growth Factor" *J. Cell. Biochem*. Suppl. 015,part F:251 (1991).

Liang et al., "Vascular Endothelial Growth Factor Induces Proliferation of Breast Cancer Cells and Inhibits the Anti-Proliferative Activity of Anti-Hormones" *Endocrine-Related Cancer* 13:905-919 (2006).

Linderholm et al., "Correlation of Vascular Endothelial Growth Factor Content with Recurrences, Survival, and First Relapse Site in Primary Node-Positive Breast Cancer Carcinoma After Adjuvant Treatment" *Journal of Clinical Oncology* 18(7):1423-1431 (Apr. 2000).

Macchiarini et al., "Relation of neovascularisation to metastasis of non-small-cell lung cancer" *Lancet* 340:145-146 (Jul. 18, 1992).

Maity et al., "Epidermal Growth Factor Receptor Transcriptionally Up-Regulates Vascular Endothelial Growth Factor Expression in Human Glioblastoma Cells via a Pathway Involving Phosphatidylinositol y-Kinase and Distinct from that Induced by Hypoxia" *Cancer Research* 60:5879-5886 (Oct. 15, 2000).

Mauer A, et al., "Phase I study of epidermal growth factor receptor (EGFR) inhibitor, e rlotinib, and vascular endothelial growth factor monoclonal antibody, bevacizumab, in recurrent and/or metastatic squamous cell carcinoma of the head and neck (SCCHN)" *Proc Am Soc Clin Oncol* 23:496 (2004).

Mercurio et al., "Non-Angiogenic Functions of VEGF in Breast Cancer" *J. Mammary Gland Biol. Neoplasia* 10:283-290 (2005).

Miller KD, et al., "Phase III trial of capecitabine (Xeloda) plus bevacizumab (Avastin) versus capecitabine alone in women with metastatic breast cancer (MBC) previously treated with an anthracycline and a taxane" *25th Annual San Antonio Breast Cancer Symposium* (Dec. 11-14 in San Antonio, Texas, 2002.

Miller KD, et al., "Phase III trial of capecitabine (Xeloda or) plus bevacizumab (Avastin) versus capecitabine alone in women with metastatic breast cancer (MBC) previously treated with an anthracycline and a taxane." *Breast Cancer Res Treat* 76:S37 (2002).

Mizukami et al., "Hypoxic Regulation of Vascular Endothelial Growth Factor through the Induction of Phosphatidylinositol 3-Kinase/Rho/ROCK and c-Myc" *The Journal of Biological Chemistry* 281(20):13957-13963 (May 19, 2006).

Muller et al., "Vascular Endothelial Growth Factor: Crystal Structure and Functional Mapping of the Kinase Domain Receptor Binding Site." *Proc. Natl. Acad. Sci. USA* 94(14):7192-7197 (Jul. 8, 1997).

Muller et al., "VEGF and the Fab fragment of a humanized neutralizing antibody: crystal structure of the complex at 2.4 A resolution and mutational analysis of the interface" *Structure* 6(9):1153-1167 (Sep. 15, 1998).

Na et al., "Overproduction of Vascular Endothelial Growth Factor Related to von Hippel-Lindau Tumor Suppressor Gene Mutations and Hypoxia-Inducible Factor-1α Expression in Renal Cell Carcinoma" *The Journal of Urology* 170:588-592 (Aug. 2003).

Nam et al., "Expression of VEGF and Brain Specific Angiogenesis Inhibitor-1 in Glioblastoma: Prognostic Significance" *Oncology Reports* 11:863-869 (2004).

Nicol at al., "Vascular Endothelial Growth Factor Expression Is Increased in Renal Cell Carcinoma" *The Journal of Urology* 157:1482-1486 (Apr. 1997).

Niedergethmann et al., "High Expression of Vascular Endothelial Growth Factor Predicts Early Recurrence and Poor Prognosis after Curative Resection for Ductal Adenocarcinoma of the Pancreas" *Pancreas* 25(2):122-129 (2002).

O'Byrne at al., "Vascular endothelial growth factor, platelet-derived endothelial cell growth factor and angiogenesis in non-small-cell lung cancer" *British Journal of Cancer* 82(8):1427-1432 (2000).

Ogata et al., "The Expression of Vascular Endothelial Growth Factor Determines the Efficacy of Post-Operative Adjuvant Chemotherapy Using Oral Fluoropyrimidines in Stage II or III Colorectal Cancer" *Oncology Reports* 15:1111-1116 (2006).

Ogawa et al., "A Novel Type of Vascular Endothelial Growth Factor, VEGF-E (NZ-7 VEGF), Preferentially Utilizes KDR/Flk-1 Receptor and Carries a Potent Mitotic Activity Without Heparin-Binding Domain." *J. Bio. Chem.* 273(47):31273-31282 (Nov. 20, 1998).

Okada et al., "Impact of Oncogenes in Tumor Angiogenesis: Mutant K-ras up-regulation of Vascular Endothelial Growth Factor/Vascular Permeability Factor is Necessary, but not Sufficient for Tumorigenicity of Human Colorectal Carcinoma Cells" *Proc. Natl. Acad. Sci.* 95:3609-3614 (Mar. 1998).

Olofsson et al., "Vascular Endothelial Growth Factor B (VEGF-B) Binds to VEGF Receptor-1 and Regulates Plasminogen Activator Activity in Endothelial Cells." *Proc. Natl. Acad. Sci. USA* 95(20):11709-11714 (Sep. 29, 1998).

Osanai et al., "Correlation Among Intratumoral Blood Flow in Breast Cancer, Clinicopathological Findings and Nottingham Prognostic Index" *Jpn J. Clin. Oncol.* 33(1):14-16 (2003).

Ottaiano et al., "Overexpression of Both CXC Chemokine Receptor 4 and Vascular Endothelial Growth Factor Proteins Predicts Early Distant Relapse in Stage II-III Colorectal Cancer Patients" *Clin. Cancer Res.* 12(9):2795-2803 (May 1, 2006).

Overmoyer B, et al., "Phase II trial of neoadjuvant docetaxel with or without bevacizumab in patients with locally advanced breast cancer" *Proc Am Soc Clin Oncol* 23:58 (2004).

Paradis et al., "Expression of vascular endothelial growth factor in renal cell carcinomas" *Virchows Arch* 436:351-356 (2000).

Park et al., "Placenta growth factor. Potentiation of vascular endothelial growth factor bioactivity, in vitro and in vivo, and high affinity binding to Flt-1 but not to Flk-1/KDR" *Journal of Biological Chemistry* 269(41):25646-25654 (1994).

Passalidou et al., "Vascular phenotype in angiogenic and non-angiogenic lung non-small cell carcinomas" *British Journal of Cancer* 86:244-249 (2002).

Pepper et al., "Lymphangiogenesis and Tumor Metastasis" *Cell Tissue Res.* 314:167-177 (2003).

Picard, Didier, "Molecular Mechanisms of Cross-Talk Between Growth Factors and Nuclear Receptor Signaling" *Pure Appl. Chem.* 75(11-12):1743-1756 (2003).

Plate et al., "Vascular Endothelial Growth Factor is a Potential Tumour Angiogenesis Factor in Human Gliomas in Vivo" *Nature* 359:845-848 (Oct. 29, 1992).

Ragaz et al., "Adverse Association of Expressed Vascular Endothelial Growth Factor (VEGF), Her2, Cox2, uPA and EMSY with long-term outcome of stage I-III breast cancer (BrCa). Results from the British Columbia Tissue Microarray Project" *Journal of Clinical Oncology* (Abstract No. 524; Jul. 15 Supplement), 2004.

Ramaswamy B, et al., "CTEP-sponsored phase II trial of bevacizumab (Avastin) in combination with docetaxel (Taxotere) in metastatic breast cancer" *Breast Cancer Res Treat* 28:S50 (2003).

Reilly et al., "Monoclonal Antibodies Directed Against Basic Fibroblast Growth Factor Which Inhibits Its Biological Activity In Vitro and In Vivo" *Biochemical and Biophysical Research Communications* 164(2):736-743 (Oct. 31, 1989).

Reinmuth et al., "Blockade of Insulin-like Growth Factor I Receptor Function Inhibits Growth and Angiogenesis of Colon Cancer" *Clinical Cancer Research* 8:3259-3269 (Oct. 2002).

Relf et al., Expression of the Angiogenic Factors Vascular Endothelial Cell Growth Factor, Acidic and Basic Fibroblast Growth Factor, Tumor Growth Factor β-1, Platelet-derived Endothelial Cell Growth Factor, Placenta Growth Factor, and Pleiotrophin in Human Primary Breast Cancer and its Relation to Cancer Research 1997.

Rini et al., "Biology and Clinical Development of Vascular Endothelial Growth Factor-Targeted Therapy in Renal Cell Carcinoma" *Journal of Clinical Oncology* 23(5):1028-1043 (Feb. 10, 2005).

Rudlowski et al., "Prognostic Significance of Vascular Endothelial Growth Factor Expression in Ovarian Cancer Patients: A Long-Term Follow-up" *Int. J. Gynecol. Cancer* (Suppl. 1) 16:183-189 (2006).

Saad et al., "Endoglin (CD105) and Vascular Endothelial Growth Factor as Prognostic Markers in Esophageal Adenocarcinoma" *Human Pathology* 36:955-961 (2005).

Saad et al., "Lymphatic Microvessel Density as Prognostic Marker in Colorectal Cancer" *Modern Pathology* 19:1317-1323 (2006).

Salomon, D. et al., "Epidermal growth factor-related peptides and their receptors in human malignancies" *Crit. Rev. Oncol./Hematol.* 19:183-232 (1995).

Sandler AB, et al., "Phase I/II trial evaluating the anti-VEGF Mab bevacizumab in combination with erlotinib, HER1/EGFR-TK inhibitor, for patients with recurrent non-small cell lung cancer" *Proc Am Soc Clin Oncol* 23:127 (2004).

Sandler et al., "Anti-Vascular Endothelial Growth Factor Monoclonals in Non-Small Cell Lung Cancer" *Clin Cancer Res.* 10:4258s-4262s (Jun. 15, 2004).

Scappaticci et al., "Analysis of wound healing and bleeding post-surgery in metastatic colorectal cancer patients treated with bevacizumab" *Gastrointestinal Cancers Symposium* (Abstract No. 235) (2004).

Schneider et al., "Angiogenesis of Breast Cancer" *Journal of Clinical Oncology* 23(8):1782-1790 (Mar. 10, 2005).

Schwartz JD, et al., "Bevacizumab in hepatocellular carcinoma in patients without metastasis and without invasion of the portal vein" *Gastrointestinal Cancers symposium* Abstract 128 (2004).

Schwartz JD, et al., "Bevacizumab in hepatocellular carcinoma in patients without metastasis and without invasion of the portal vein" *Gastrointestinal Cancers Symposium* (Jan. 22-24, San Francisco, California) (2004).

Senger et al., "Tumor cells secrete a vascular permeability factor that promotes accumulation of ascites fluid" *Science* 219(4587):983-985 (Feb. 25, 1983).

Seo et al., "High Expression of Vascular Endothelial Growth Factor Is Associated with Liver Metastasis and a Poor Prognosis for Patients with Ductal Pancreatic Adenocarcinoma" *Cancer* 88(10):2239-2245 (May 15, 2000).

Shibuya, "Role of VEGF-FLT Receptor System in Normal and Tumor Angiogenesis" *Advances in Cancer Research* 67:281-316 (1995).

Shweiki et al., "Vascular endothelial growth factor induced by hypoxia may mediate hypoxia-initiated angiogenesis" *Nature* 359:843-845 (1992).

Stefanou et al., "Expression of vascular endothelial growth factor (VEGF) and association with microvessel density in small-cell and non-small-cell lung carcinomas" *Histol Histopathol* 19:37-42 (2004).

Stimpfl, "Vascular Endothelial Growth Factor Splice Variants and Their Prognostic Value in Breast and Ovarian Cancer" *Clinical Cancer Research* 8:2253-2259 (Jul. 2002).

Sturk et al., "Angiogenesis", Chapter 12, pp. 231-248.

Takahashi et al., "Markedly Increased Amounts of Messenger RNAs for Vascular Endothelial Growth Factor and Placenta Growth Factor in Renal Cell Carcinoma Associated with Angiogenesis" *Cancer Research* 54:4233-4237 (Aug. 1, 1994).

Takahashi et al., "The Angiogenic Switch of Human Colon Cancer Occurs Simultaneous to Initiation of Invasion" *Oncology Reports* 10:9-13 (2003).

Tanigawa et al., "Tumor Angiogenesis and Mode of Metastasis in Patients with Colorectal Cancer" *Cancer Research* 57:1043-1046 (Mar. 15, 1997).

Terman et al., "Identification of a New Endothelial Cell Growth Factor Receptor Tyrosine Kinase." *Oncogene.* 6:1677-1683 (1991).

Terman et al., "Identification of the KDR Tyrosine Kinase as a Receptor for Vascular Endothelial Cell Growth Factor." *Biochem. & Biophys. Res. Comm.* 187:1579-1586 (1992).

Thakker et al., "The Role of Phosphatidylinositol 3-Kinase in Vascular Endothelial Growth Factor Signaling" *The Journal of Biological Chemistry* 274(15):10002-10007 (Apr. 9, 1999).

Tischer et al., "Vascular Endothelial Growth Factor: A New Member of the Platelet-Derived Growth Factor Gene Family" *Biochem. & Biophys. Res. Comm.* 165(3):1198-1206 (1989).

Toi et al., "Tumor Angiogenesis in Breast Cancer: Its Importance as a Prognostic Indicator and the Association with Vascular Endothelial Growth Factor Expression" *Breast Cancer Research and Treatment* pp. 193-204 (1995).

Tomisawa et al., "Expression Pattern of Vascular Endothelial Growth Factor Isoform is Closely Correlated with Tumor Stage and Vascularisation in Renal Cell Carcinoma" *Eurpean Journal of Cancer* 35(1):133-137 (1999).

Tsuchiya et al., "Quantitative Analysis of Gene Expressions of Vascular Endothelial Growth Factor-Related Factors and Their Receptors in Renal Cell Carcinoma" *Tohoku J Exp Med.* 195:101-113 (2001).

Ushijima et al., "High vascularity in the peripheral region of non-small cell lung cancer tissue is associated with tumor progression" *Lung Cancer* 34:233-241 (2001).

Valtola et al., "VEGFR-3 and Its Ligand VEGF-C Are Associated with Angiogenesis in Breast Cancer" *American Journal of Pathology* 154(5):1381-1390 (May 1999).

Van der Auwera et al., "Increased Angiogenesis and Lymphangiogenesis in Inflammatory versus Noninflammatory Breast Cancer by Real-Time Reverse Transcriptase-PCR Gene Expression Quantification" *Clinical Cancer Research* 10:7965-7971 (Dec. 1, 2004).

Veronese and O'Dwyer, "Monoclonal antibodies in the treatment of colorectal cancer" *European Journal of Cancer* 40:1292-1301 (2004).

Warren et al., "Induction of Vascular Endothelial Growth Factor by Insulin-like Growth Factor 1 in Colorectal Carcinoma" *The Journal of Biological Chemistry* 271(46):29483-29488 (Nov. 15, 1996).

Wedam SB, et al., "A pilot study to evaluate response and angiogenesis after treatment with bevacizumab in patients with inflammatory breast cancer" *Proc Am Soc Clin Oncol* 23:21 (2004).

Weidner et al., "Tumor angiogenesis and metastasis—correlation in invasive breast carcinoma " *New England J. of Medicine* 324(1):1-8 (1991).

Weigand et al., "Autocrine Vascular Endothelial Growth Factor Signalling in Breast Cancer. Evidence from Cell Lines and Primary Breast Cancer Cultures in Vitro" *Angiogenesis* 8:197-204 (2005).

Willett et al., "Direct evidence that the VEGF-specific antibody bevacizumab has antivascular effects in human rectal cancer" *Nature Medicine* pp. 1-3 (Jan. 25, 2004).

Willett et al., "Phase I study of neoadjuvant bevacizumab, 5-fluorouracil, and radiation therapy followed by surgery for patients with primary rectal cancer" *American Society of Clinical Oncology Meeting Proceedings* (Abstract #3589) 23 (2004).

Yamazaki et al., "Tumor Angiogenesis in Human Lung Adenocarcinoma" *Cancer* 74:2245-2250 (1994).

Yang et al., "ErbB2 Overexpression Correlates with Increased Expression of Vascular Endothelial Growth Factors A, C and D in Human Breast Carcinoma" *Cancer* 94(11):2855-2861 (Jun. 1, 2002).

Yang JC, et al., "A randomized trial of Bevacizumab, an anti-vascular endothelial growth factor antibody, for metastatic renal cancer" *N. Engl J Med* 349:427-434 (2003).

Yao et al., "Inhibition of Cyclooxygenase-2 by Rofecoxib Attenuates the Growth and Metastatic Potential of Colorectal Carcinoma in Mice" *Cancer Research* 63:586-592 (Feb. 1, 2003).

Yarden et al., "Untangling the ErbB signalling network" *Nat. Rev. Mol. Cell. Biol.* 2(2) :127-137 (Feb. 2001).

Yeh et al., "Autocrine IL-6-induced Stat3 activation contributes to the pathogenesis of lung adenocarcinoma and malignant pleural effusion" *Oncogene* 25:4300-4309 (2006).

Yildiz et al., "Prognostic value of the expression of Ki-67, CD44 and vascular endothelial growth factor, and microvessel invasion, in renal cell carcinoma" *BJU International* 93:1087-1093 (2004).

Yoshiji et al., "Expression of Vascular Endothelial Growth Factor, Its Receptor, and Other Angiogenic Factors in Human Breast Cancer" *Cancer Research* 56:2013-2016 (May 1, 1996).

Yuan et al., "Correlation of Total VEGF mRNA and Protein Expression With Histologic Type, Tumor Angiogenesis, Patient Survival and Timing of Relapse in Non-Small-Cell Lung Cancer" *Int. J. Cancer (Pred. Oncol.)* 89:475-483 (2000).

Zeng et al., "Vascualr Permeability Factor (VPF) / Vascular Endothelial Growth Factor (VEGF) Receptor-1 Down-modulates VPF/VEGF Receptor-2-mediated Endothelial Cell Proliferation, but not Migration, through Phosphatidylinositol 3-Kinase-dependent Pathways" *Journal of Biological Chemistry* 276:26969-26979 (2001).

Zlobec et al., "VEGF as a Predictive Marker of Rectal Tumor Response to Preoperative Radiotherapy" *Cancer* 104(11):2517-2521 (Dec. 1, 2005).

Shaheen et al., "Effects of an antibody to vascular endothelial growth factor receptor-2 on survival, tumor vascularity, and apoptosis in a murine model of colon carcinomatosis" *International Journal of Oncology* 18:221-226 (2001).

Kim et al., "Phase II study of capecitabine plus cisplatin as first-line chemotherapy in advanced gastric cancer" *Annals of Oncology* 13:1893-1898 (2002).

\* cited by examiner

TREATMENT WITH ANTI-VEGF ANTIBODIES

This is a continuation application claiming priority to U.S. application Ser. No. 10/857,249, filed May 28, 2004, now abandoned, which is a non-provisional application claiming priority to U.S. provisional Application No. 60/474,480, filed May 30, 2003, the contents of which are incorporated herein by reference.

FIELD OF THE INVENTION

This invention relates in general to treatment of human diseases and pathological conditions. More specifically, the invention relates to anti-angiogenesis therapy of cancer, either alone or in combination with other anti-cancer therapies.

BACKGROUND OF THE INVENTION

Cancer remains to be one of the most deadly threats to human health. In the U.S., cancer affects nearly 1.3 million new patients each year, and is the second leading cause of death after heart disease, accounting for approximately 1 in 4 deaths. It is also predicted that cancer may surpass cardiovascular diseases as the number one cause of death within 5 years. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making timely detection and treatment extremely difficult. Furthermore, cancers can arise from almost any tissue in the body through malignant transformation of one or a few normal cells within the tissue, and each type of cancer with particular tissue origin differs from the others.

Current methods of cancer treatment are relatively non-selective. Surgery removes the diseased tissue; radiotherapy shrinks solid tumors; and chemotherapy kills rapidly dividing cells. Chemotherapy, in particular, results in numerous side effects, in some cases so severe as to limit the dosage that can be given and thus preclude the use of potentially effective drugs. Moreover, cancers often develop resistance to chemotherapeutic drugs.

Thus, there is an urgent need for specific and more effective cancer therapies.

Angiogenesis is an important cellular event in which vascular endothelial cells proliferate, prune and reorganize to form new vessels from preexisting vascular network. There are compelling evidences that the development of a vascular supply is essential for normal and pathological proliferative processes (Folkman and Klagsbrun (1987) Science 235:442-447). Delivery of oxygen and nutrients, as well as the removal of catabolic products, represent rate-limiting steps in the majority of growth processes occurring in multicellular organisms. Thus, it has been generally assumed that the vascular compartment is necessary, not only for organ development and differentiation during embryogenesis, but also for wound healing and reproductive functions in the adult.

Angiogenesis is also implicated in the pathogenesis of a variety of disorders, including but not limited to, tumors, proliferative retinopathies, age-related macular degeneration, rheumatoid arthritis (RA), and psoriasis. Angiogenesis is essential for the growth of most primary tumors and their subsequent metastasis. Tumors can absorb sufficient nutrients and oxygen by simple diffusion up to a size of 1-2 mm, at which point their further growth requires the elaboration of vascular supply. This process is thought to involve recruitment of the neighboring host mature vasculature to begin sprouting new blood vessel capillaries, which grow towards, and subsequently infiltrate, the tumor mass. In addition, tumor angiogenesis involve the recruitment of circulating endothelial precursor cells from the bone marrow to promote neovascularization. Kerbel (2000) *Carcinogenesis* 21:505-515; Lynden et al. (2001) *Nat. Med.* 7:1194-1201.

While induction of new blood vessels is considered to be the predominant mode of tumor angiogenesis, recent data have indicated that some tumors may grow by co-opting existing host blood vessels. The co-opted vasculature then regresses, leading to tumor regression that is eventually reversed by hypoxia-induced angiogenesis at the tumor margin. Holash et al. (1999) *Science* 284:1994-1998.

In view of the remarkable physiological and pathological importance of angiogenesis, much work has been dedicated to the elucidation of the factors capable of regulating this process. It is suggested that the angiogenesis process is regulated by a balance between pro- and anti-angiogenic molecules, and is derailed in various diseases, especially cancer. Carmeliet and Jain (2000) *Nature* 407:249-257.

Vascular endothelial cell growth factor (VEGF), which is also termed VEGF-A or vascular permeability factor (VPF), has been reported as a pivotal regulator of both normal and abnormal angiogenesis. Ferrara and Davis-Smyth (1997) *Endocrine Rev.* 18:4-25; Ferrara (1999) *J. Mol. Med.* 77:527-543. Compared to other growth factors that contribute to the processes of vascular formation, VEGF is unique in its high specificity for endothelial cells within the vascular system. VEGF is essential for embryonic vasculogenesis and angiogenesis. Carmeliet et al. (1996) *Nature* 380:435-439; Ferrara et al. (1996) *Nature* 380:439-442. Furthermore, VEGF is required for the cyclical blood vessel proliferation in the female reproductive tract and for bone growth and cartilage formation. Ferrara et al. (1998) *Nature Med.* 4:336-340; Gerber et al. (1999) *Nature Med.* 5:623-628.

In addition to being an angiogenic factor in angiogenesis and vasculogenesis, VEGF, as a pleiotropic growth factor, exhibits multiple biological effects in other physiological processes, such as endothelial cell survival, vessel permeability and vasodilation, monocyte chemotaxis and calcium influx. Ferrara and Davis-Smyth (1997), supra. Moreover, recent studies have reported mitogenic effects of VEGF on a few non-endothelial cell types, such as retinal pigment epithelial cells, pancreatic duct cells and Schwann cells. Guerrin et al. (1995) *J. Cell Physiol.* 164:385-394; Oberg-Welsh et al. (1997) *Mol. Cell. Endocrinol.* 126:125-132; Sondell et al. (1999) *J. Neurosci.* 19:5731-5740.

Substantial evidence also implicates VEGF's critical role in the development of conditions or diseases that involve pathological angiogenesis. The VEGF mRNA is overexpressed by the majority of human tumors examined (Berkman et al. *J Clin Invest* 91:153-159 (1993); Brown et al. *Human Pathol.* 26:86-91 (1995); Brown et al. *Cancer Res.* 53:4727-4735 (1993); Mattern et al. *Brit. J. Cancer.* 73:931-934 (1996); and Dvorak et al. *Am J. Pathol.* 146:1029-1039 (1995)). Also, the concentration of VEGF in eye fluids are highly correlated to the presence of active proliferation of blood vessels in patients with diabetic and other ischemia-related retinopathies (Aiello et al. *N. Engl. J. Med.* 331:1480-1487 (1994)). Furthermore, recent studies have demonstrated the localization of VEGF in choroidal neovascular membranes in patients affected by AMD (Lopez et al. *Invest. Ophtalmo. Vis. Sci.* 37:855-868 (1996)).

Given its central role in promoting tumor growth, VEGF provides an attractive target for therapeutic intervention. Indeed, a variety of therapeutic strategies aimed at blocking VEGF or its receptor signaling system are currently being developed for the treatment of neoplastic diseases. Rosen (2000) *Oncologist* 5:20-27; Ellis et al. (2000) *Oncologist* 5:11-15; Kerbel (2001) *J. Clin. Oncol.* 19:45 S-51S. So far, VEGFVEGF receptor blockade by monoclonal antibodies and inhibition of receptor signaling by tyrosine kinase inhibitors are the best studied approaches. VEGFR-1 ribozymes, VEGF toxin conjugates, and soluble VEGF receptors are also being investigated.

The anti-VEGF antibody "Bevacizumab (BV)", also known as "rhuMAb VEGF" or "Avastin™" is a recombinant humanized anti-VEGF monoclonal antibody generated according to Presta et al. (1997) *Cancer Res.* 57:4593-4599. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 daltons and is glycosylated. Bevacizumab is being investigated clinically for treating various cancers, and some early stage trials have shown promising results. Kerbel (2001) *J. Clin. Oncol.* 19:45 S-51S; De Vore et al. (2000) *Proc. Am. Soc. Clin. Oncol.* 19:485a; Johnson et al. (2001) *Proc. Am. Soc. Clin. Oncol.* 20:315a; Kabbinavar et al. (2003) *J. Clin. Oncol.* 21:60-65.

SUMMARY OF THE INVENTION

The present invention concerns methods of using anti-VEGF antibody for treating diseases and pathological conditions. In particular, the invention provides an effective approach for treating cancers, partially based on the unexpected results that adding anti-VEGF antibody to a standard chemotherapy results in statistically significant and clinically meaningful improvements among cancer patients.

Accordingly, in one aspect, the invention provides a method of treating cancer in a human patient, comprising administering to the patient effective amounts of an anti-VEGF antibody and an anti-neoplastic composition, wherein said anti-neoplastic composition comprises at least one chemotherapeutic agent.

The cancer amendable for treatment by the present invention include, but not limited to, carcinoma, lymphoma, blastoma, sarcoma, and leukemia or lymphoid malignancies. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, melanoma, ovarian cancer, mesothelioma, and multiple myeloma. More preferably, the cancer is colorectal cancer. The cancerous conditions amendible for treatment of the invention include metastatic cancers. The method of the present invention is particularly suitable for the treatment of vascularized tumors.

Any chemotherapeutic agent exhibiting anticancer activity can be used according to the present invention. Preferably, the chemotherapeutic agent is selected from the group consisting of alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitor, interferons, platinum cooridnation complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. More preferably, the chemotherapeutic agent is selected from the group consisting of 5-fluorouracil (5-FU), leucovorin (LV), irenotecan, oxaliplatin, capecitabine, paclitaxel and doxetaxel. Two or more chemotherapeutic agents can be used in a cocktail to be administered in combination with administration of the anti-VEGF antibody. One preferred combination chemotherapy is fluorouracil-based, comprising 5-FU and one or more other chemotherapeutic agent(s). Suitable dosing regimens of combination chemotherapies are known in the art and described in, for example, Saltz et al. (1999) *Proc ASCO* 18:233a and Douillard et al. (2000) *Lancet* 355: 1041-7.

In one aspect, the present invention provides a method for increasing the duration of survival of a human patient having cancer, comprising administering to the patient effective amounts of an anti-VEGF antibody composition and an anti-neoplastic composition, wherein said anti-neoplastic composition comprises at least one chemotherapeutic agent, whereby the co-administration of the anti-VEGF antibody and the anti-neoplastic composition effectively increases the duration of survival.

In another aspect, the present invention provides a method for increasing the progression free survival of a human patient having cancer, comprising administering to the patient effective amounts of an anti-VEGF antibody composition and an anti-neoplastic composition, wherein said anti-neoplastic composition comprises at least one chemotherapeutic agent, whereby the co-administration of the anti-VEGF antibody and the anti-neoplastic composition effectively increases the duration of progression free survival.

Furthermore, the present invention provides a method for treating a group of human patients having cancer, comprising administering to the patient effective amounts of an anti-VEGF antibody composition and an anti-neoplastic composition, wherein said anti-neoplastic composition comprises at least one chemotherapeutic agent, whereby the co-administration of the anti-VEGF antibody and the anti-neoplastic composition effectively increases the response rate in the group of patients.

In yet another aspect, the present invention provides a method for increasing the duration of response of a human patient having cancer, comprising administering to the patient effective amounts of an anti-VEGF antibody composition and an anti-neoplastic composition, wherein said anti-neoplastic composition comprises at least one chemotherapeutic agent, whereby the co-administration of the anti-VEGF antibody and the anti-neoplastic composition effectively increases the duration of response.

The invention also provides a method of treating a human patient susceptible to or diagnosed with colorectal cancer, comprising administering to the patient effective amounts of an anti-VEGF antibody. The colorectal cancer can be metastatic. The anti-VEGF antibody treatment can be further combined with a standard chemotherapy for colorectal cancer such as the Saltz (5-FU/LV/irinotecan) regimen described by Saltz et al. (1999).

In one preferred embodiment, the invention provides a method of treating a human patient or a group of human patients having metastatic colorectal cancer, comprising administering to the patient effective amounts of an anti-VEGF antibody composition and an anti-neoplastic composition, wherein said anti-neoplastic composition comprises at least one chemotherapeutic agent, whereby the co-administration of the anti-VEGF antibody and the anti-neoplastic composition results in statistically significant and clinically meaningful improvement of the treated patient as measured by the duration of survival, progression free survival, response rate or duration of response. Preferably, the anti-neoplastic composition is a fluorouracil based combination regimen. More preferably the combination regimen comprises 5-FU+leucovorin, 5-FU+leucovorin+irinotecan (IFL), or 5-FU+leucorvin+oxaliplatin (FOLFOX).

The invention provides an article of manufacture comprising a container, a composition within the container comprising an anti-VEGF antibody and a package insert instructing the user of the composition to administer to a cancer patient the anti-VEGF antibody composition and an anti-neoplastic composition comprising at least one chemotherapeutic agent.

The invention also provides a kit for treating cancer in a patient comprising a package comprising an anti-VEGF antibody composition and instructions for using the anti-VEGF antibody composition and an anti-neoplastic composition comprising at least one chemotherapeutic agent for treating cancer in a patient.

DETAILED DESCRIPTION OF THE PREFERRED EMBODIMENTS

I. Definitions

Figure 1:
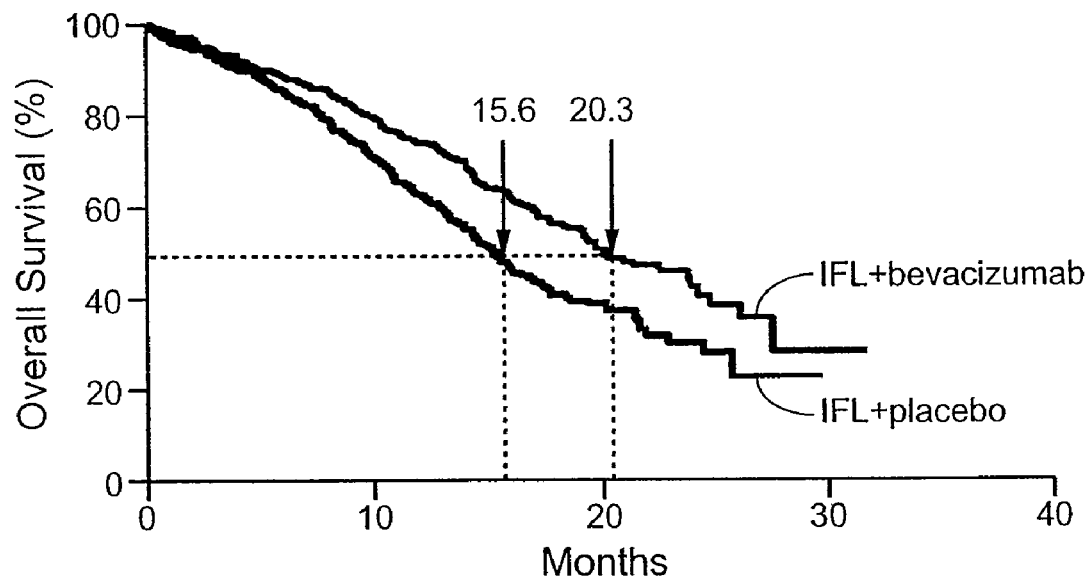
FIG. 1 represents Kaplan-Meier estimates of survival. The median duration of survival (indicated by the dotted lines) was 20.3 months in the group given irinotecan, fluorouracil, and leucovorin (IFL) plus bevacizumab, as compared with 15.6 months in the group given IFL plus placebo, corresponding to a hazard ratio for death of 0.66 (P<0.001).

The terms "VEGF" and "VEGF-A" are used interchangeably to refer to the 165-amino acid vascular endothelial cell growth factor and related 121-, 189-, and 206-amino acid vascular endothelial cell growth factors, as described by Leung et al. *Science,* 246:1306 (1989), and Houck et al. *Mol. Endocrin.,* 5:1806 (1991), together with the naturally occurring allelic and processed forms thereof. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

An "anti-VEGF antibody" is an antibody that binds to VEGF with sufficient affinity and specificity. Preferably, the anti-VEGF antibody of the invention can be used as a therapeutic agent in targeting and interfering with diseases or conditions wherein the VEGF activity is involved. An anti-VEGF antibody will usually not bind to other VEGF homologues such as VEGF-B or VEGF-C, nor other growth factors such as PlGF, PDGF or bFGF. A preferred anti-VEGF antibody is a monoclonal antibody that binds to the same epitope as the monoclonal anti-VEGF antibody A4.6.1 produced by hybridoma ATCC HB 10709. More preferably the anti-VEGF antibody is a recombinant humanized anti-VEGF monoclonal antibody generated according to Presta et al. (1997) Cancer Res. 57:4593-4599, including but not limited to the antibody known as bevacizumab (BV; Avastin™).

A "VEGF antagonist" refers to a molecule capable of neutralizing, blocking, inhibiting, abrogating, reducing or interfering with VEGF activities including its binding to one or more VEGF receptors. VEGF antagonists include anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases.

Throughout the present specification and claims, the numbering of the residues in an immunoglobulin heavy chain is that of the EU index as in Kabat et al., *Sequences of Proteins of Immunological Interest,* 5th Ed. Public Health Service, National Institutes of Health, Bethesda, Md. (1991), expressly incorporated herein by reference. The "EU index as in Kabat" refers to the residue numbering of the human IgG1 EU antibody.

A "native sequence" polypeptide comprises a polypeptide having the same amino acid sequence as a polypeptide derived from nature. Thus, a native sequence polypeptide can have the amino acid sequence of naturally-occurring polypeptide from any mammal. Such native sequence polypeptide can be isolated from nature or can be produced by recombinant or synthetic means. The term "native sequence" polypeptide specifically encompasses naturally-occurring truncated or secreted forms of the polypeptide (e.g., an extracellular domain sequence), naturally-occurring variant forms (e.g., alternatively spliced forms) and naturally-occurring allelic variants of the polypeptide.

A polypeptide "variant" means a biologically active polypeptide having at least about 80% amino acid sequence identity with the native sequence polypeptide. Such variants include, for instance, polypeptides wherein one or more amino acid residues are added, or deleted, at the N- or C-terminus of the polypeptide. Ordinarily, a variant will have at least about 80% amino acid sequence identity, more preferably at least about 90% amino acid sequence identity, and even more preferably at least about 95% amino acid sequence identity with the native sequence polypeptide.

The term "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments (see below) so long as they exhibit the desired biological activity.

Unless indicated otherwise, the expression "multivalent antibody" is used throughout this specification to denote an antibody comprising three or more antigen binding sites. The multivalent antibody is preferably engineered to have the three or more antigen binding sites and is generally not a native sequence IgM or IgA antibody.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., *Nature* 341, 544-546 (1989)) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., *Science* 242:423-426 (1988); and Huston et al., *PNAS (USA)* 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., *Proc. Natl. Acad. Sci. USA*, 90:6444-6448 (1993)); (xi) "linear antibodies" comprising a pair of tandem Fd segments (VH-CH$_1$-VH-CH$_1$) which, together with complementary light chain polypeptides, form a pair of antigen binding regions (Zapata et al. *Protein Eng.* 8(10):1057-1062 (1995); and U.S. Pat. No. 5,641,870).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) or Marks et al., *J. Mol. Biol.* 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g. murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. *Nature Biotechnology* 14:309-314 (1996): Sheets et al. *PNAS (USA)* 95:6157-6162 (1998)); Hoogenboom and Winter, *J. Mol. Biol.*, 227:381 (1991); Marks et al., *J. Mol. Biol.*, 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., *Bio/Technology* 10: 779-783 (1992); Lonberg et al., *Nature* 368: 856-859 (1994); Morrison, *Nature* 368:812-13 (1994); Fishwild et al., *Nature Biotechnology* 14: 845-51 (1996); Neuberger, *Nature Biotechnology* 14: 826 (1996); Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same. For the multimeric antibodies herein, the number of functional antigen binding sites can be evaluated using ultracentrifugation analysis as described in Example 2 below. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

An antibody having a "biological characteristic" of a designated antibody is one which possesses one or more of the biological characteristics of that antibody which distinguish it from other antibodies that bind to the same antigen.

In order to screen for antibodies which bind to an epitope on an antigen bound by an antibody of interest, a routine cross-blocking assay such as that described in *Antibodies, A Laboratory Manual*, Cold Spring Harbor Laboratory, Ed Harlow and David Lane (1988), can be performed.

An "agonist antibody" is an antibody which binds to and activates a receptor. Generally, the receptor activation capability of the agonist antibody will be at least qualitatively similar (and may be essentially quantitatively similar) to a native agonist ligand of the receptor. An example of an agonist antibody is one which binds to a receptor in the TNF receptor superfamily and induces apoptosis of cells expressing the TNF receptor. Assays for determining induction of apoptosis are described in WO98/51793 and WO99/37684, both of which are expressly incorporated herein by reference.

A "disorder" is any condition that would benefit from treatment with the antibody. This includes chronic and acute disorders or diseases including those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

"Treatment" refers to both therapeutic treatment and prophylactic or preventative measures. Those in need of treatment include those already with the disorder as well as those in which the disorder is to be prevented.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The term "mammalian host" as used herein refers to any compatible transplant recipient. By "compatible" is meant a mammalian host that will accept the donated graft. Preferably, the host is human. If both the donor of the graft and the host are human, they are preferably matched for HLA class II antigens so as to improve histocompatibility.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

The term "anti-neoplastic composition" refers to a composition useful in treating cancer comprising at least one active therapeutic agent capable of inhibiting or preventing tumor growth or function, and/or causing destruction of tumor cells. Therapeutic agents suitable in an anti-neoplastic composition for treating cancer include, but not limited to, chemotherapeutic agents, radioactive isotopes, toxins, cytokines such as interferons, and antagonistic agents targeting cytokines, cytokine receptors or antigens associated with tumor cells. For example, therapeutic agents useful in the present invention can be antibodies such as anti-HER2 antibody and anti-CD20 antibody, or small molecule tyrosine kinase inhibitors such as VEGF receptor inhibitors and EGF receptor inhibitors. Preferably the therapeutic agent is a chemotherapeutic agent.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON.toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMI- DEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor; hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery*, Borchardt et al. (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The term "intravenous infusion" refers to introduction of a drug into the vein of an animal or human patient over a period of time greater than approximately 5 minutes, preferably between approximately 30 to 90 minutes, although, according to the invention, intravenous infusion is alternatively administered for 10 hours or less.

The term "intravenous bolus" or "intravenous push" refers to drug administration into a vein of an animal or human such that the body receives the drug in approximately 15 minutes or less, preferably 5 minutes or less.

The term "subcutaneous administration" refers to introduction of a drug under the skin of an animal or human patient, preferable within a pocket between the skin and underlying tissue, by relatively slow, sustained delivery from a drug receptacle. The pocket may be created by pinching or drawing the skin up and away from underlying tissue.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is preferably less than approximately 15 minutes, more preferably less than 5 minutes, and most preferably less than 60 seconds. Administration is preferably within a pocket between the skin and underlying tissue, where the pocket is created, for example, by pinching or drawing the skin up and away from underlying tissue.

An "angiogenic factor" is a growth factor which stimulates the development of blood vessels. The preferred angiogenic factor herein is Vascular Endothelial Growth Factor (VEGF).

The word "label" when used herein refers to a detectable compound or composition which is conjugated directly or indirectly to the polypeptide. The label may be itself be detectable (e.g., radioisotope labels or fluorescent labels) or, in the case of an enzymatic label, may catalyze chemical alteration of a substrate compound or composition which is detectable.

An "isolated" nucleic acid molecule is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

II. Production of Anti-VEGF Antibodies

A. Antibody Preparation (i) VEGF Antigen

Means for preparing and characterizing antibodies are well known in the art. A description follows as to exemplary techniques for the production of anti-VEGF antibodies used in accordance with the present invention. The VEGF antigen to be used for production of antibodies may be, e.g., the $VEGF_{165}$ molecule as well as other isoforms of VEGF or a fragment thereof containing the desired epitope. Other forms of VEGF useful for generating anti-VEGF antibodies of the invention will be apparent to those skilled in the art.

Human VEGF was obtained by first screening a cDNA library prepared from human cells, using bovine VEGF cDNA as a hybridization probe. Leung et al. (1989) *Science*, 246:1306. One cDNA identified thereby encodes a 165-amino acid protein having greater than 95% homology to bovine VEGF; this 165-amino acid protein is typically referred to as human VEGF (hVEGF) or $VEGF_{165}$. The mitogenic activity of human VEGF was confirmed by expressing the human VEGF cDNA in mammalian host cells. Media conditioned by cells transfected with the human VEGF cDNA promoted the proliferation of capillary endothelial cells, whereas control cells did not. Leung et al. (1989) *Science*, supra.

Although a vascular endothelial cell growth factor could be isolated and purified from natural sources for subsequent therapeutic use, the relatively low concentrations of the protein in follicular cells and the high cost, both in terms of effort and expense, of recovering VEGF proved commercially unavailing. Accordingly, further efforts were undertaken to clone and express VEGF via recombinant DNA techniques. (See, e.g., Ferrara (1995) *Laboratory Investigation* 72:615-618, and the references cited therein).

VEGF is expressed in a variety of tissues as multiple homodimeric forms (121, 145, 165, 189, and 206 amino acids per monomer) resulting from alternative RNA splicing. $VEGF_{121}$ is a soluble mitogen that does not bind heparin; the longer forms of VEGF bind heparin with progressively higher affinity. The heparin-binding forms of VEGF can be cleaved in the carboxy terminus by plasmin to release a diffusible form(s) of VEGF. Amino acid sequencing of the carboxy terminal peptide identified after plasmin cleavage is $Arg_{110}$-$Ala_{111}$. Amino terminal "core" protein, VEGF (1-110) isolated as a homodimer, binds neutralizing monoclonal antibodies (such as the antibodies referred to as 4.6.1 and 3.2E3.1.1) and soluble forms of VEGF receptors with similar affinity compared to the intact $VEGF_{165}$ homodimer.

Several molecules structurally related to VEGF have also been identified recently, including placenta growth factor (PlGF), VEGF-B, VEGF-C, VEGF-D and VEGF-E. Ferrara and Davis-Smyth (1987) Endocr. Rev., supra; Ogawa et al. (1998) *J. Biological Chem.* 273:31273-31281; Meyer et al. (1999) *EMBO J.*, 18:363-374. A receptor tyrosine kinase, Flt-4 (VEGFR-3), has been identified as the receptor for VEGF-C and VEGF-D. Joukov et al. (1996) *EMBO. J.* 15:1751; Lee et al. (1996) *Proc. Natl. Acad. Sci. USA* 93:1988-1992; Achen et al. (1998) *Proc. Natl. Acad. Sci. USA* 95:548-553. VEGF-C has recently been shown to be involved in the regulation of lymphatic angiogenesis. Jeltsch et al. (1997) *Science* 276:1423-1425.

Two VEGF receptors have been identified, Flt-1 (also called VEGFR-1) and KDR (also called VEGFR-2). Shibuya et al. (1990) *Oncogene* 8:519-527; de Vries et al. (1992) *Science* 255:989-991; Terman et al. (1992) *Biochem. Biophys. Res. Commun.* 187:1579-1586. Neuropilin-1 has been shown to be a selective VEGF receptor, able to bind the heparin-binding VEGF isoforms (Soker et al. (1998) *Cell* 92:735-45). Both Flt-I and KDR belong to the family of receptor tyrosine kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich (1988) *Ann. Rev. Biochem.* 57:433-478; Ullrich and Schlessinger (1990) *Cell* 61:243-254). The intrinsic function of RTKs is activated upon ligand binding, which results in phosphorylation of the receptor and multiple cellular substrates, and subsequently in a variety of cellular responses (Ullrich & Schlessinger (1990) *Cell* 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see, Schlessinger and Ullrich (1992) *Neuron* 9: 1-20. Structurally, both Flt-1 and KDR have seven immunoglobulin-like domains in the extracellular domain, a single transmembrane region, and a consensus tyrosine kinase sequence which is interrupted by a kinase-insert domain. Matthews et al. (1991) *Proc. Natl. Acad. Sci. USA* 88:9026-9030; Terman et al. (1991) *Oncogene* 6:1677-1683.

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.,* 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., *Nature,* 348: 552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iv) Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239: 1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and Duchosal et al. Nature 355:258 (1992). Human antibodies can also be derived from phage-display libraries (Hoogenboom et al., J. Mol. Biol., 227:381 (1991); Marks et al., J. Mol. Biol., 222:581-597 (1991); Vaughan et al. Nature Biotech 14:309 (1996)).

(v) Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229: 81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form $F(ab')_2$ fragments (Carter et al., Bio/Technology 10: 163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(vi) Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA);

BsAbs for targeting immune complexes to cell surface receptors such as anti-low density lipoprotein (LDL)/anti-Fc receptor (e.g. FcγRI, FcγRII or FcγRIII); BsAbs for use in therapy of infectious diseases such as anti-CD3/anti-herpes simplex virus (HSV), anti-T-cell receptor:CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986). According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the VEGF receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

(vii) Effector Function Engineering

It may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

(viii) Immunoconjugates

The invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. A variety of radionuclides are available for the production of radioconjugate antibodies. Examples include $^{212}Bi$, $^{131}I$, $^{131}In$, $^{90}Y$ and $^{186}Re$.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(ix) Immunoliposomes

The antibody disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent (such as Doxorubicin) is optionally contained within the liposome. See Gabizon et al. *J. National Cancer Inst.* 81(19)1484 (1989)

(x) Antibody Dependent Enzyme Mediated Prodrug Therapy (ADEPT)

The antibody of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to convert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes of this invention can be covalently bound to the antibody by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature,* 312: 604-608 (1984)).

(xi) Antibody-Salvage Receptor Binding Epitope Fusions.

In certain embodiments of the invention, it may be desirable to use an antibody fragment, rather than an intact antibody, to increase tumor penetration, for example. In this case, it may be desirable to modify the antibody fragment in order to increase its serum half life. This may be achieved, for example, by incorporation of a salvage receptor binding epitope into the antibody fragment (e.g. by mutation of the appropriate region in the antibody fragment or by incorporating the epitope into a peptide tag that is then fused to the antibody fragment at either end or in the middle, e.g., by DNA or peptide synthesis).

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment.

(xii) Other Covalent Modifications of the Antibody

Covalent modifications of the antibody are included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T.E. Creighton, *Proteins: Structure and Molecular Properties*, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, *CRC Crit. Rev. Biochem.*, pp. 259-306 (1981).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al. *Arch. Biochem. Biophys.* 259:52 (1987) and by Edge et al. *Anal. Biochem.,* 118:131 (1981). Enzymatic cleavage of carbohydrate moieties on antibodies can be achieved by the use of a variety of endo- and exo-glycosidases as described by Thotakura et al. *Meth. Enzymol.* 138:350 (1987).

Another type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

B. Vectors, Host Cells and Recombinant Methods

The anti-VEGF antibody of the invention can be produced recombinantly, using techniques and materials readily obtainable.

For recombinant production of an anti-VEGF antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, α factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(iv) Promoter Component

Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419, 446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv (1982) *Nature* 297:17-18 on enhancing elements for activation of eukaryotic promoters. The enhancer may be spliced into the vector at a position 5' or 3' to the antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Antibody Purification

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the anti-VEGF antibody and contaminants may be subjected to low pH hydrophobic interaction chromatography using an elution buffer at a pH between about 2.5-4.5, preferably performed at low salt concentrations (e.g., from about 0-0.25M salt).

III. Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Preferred lyophilized anti-VEGF antibody formulations are described in WO 97/04801, expressly incorporated herein be reference.

The formulation herein may also contain more than one active compound as necessary for the particular indication being treated, preferably those with complementary activities that do not adversely affect each other. For example, it may be desirable to further provide antibodies which bind to EGFR, VEGF (e.g. an antibody which binds a different epitope on VEGF), VEGFR, or ErbB2 (e.g., Herceptin®) in the one formulation. Alternatively, or in addition, the composition may comprise a cytotoxic agent, cytokine, growth inhibitory agent and/or small molecule VEGFR antagonist. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

IV. Therapeutic Uses of Anti-VEGF Antibodies

It is contemplated that, according to the present invention, the anti-VEGF antibodies may be used to treat various neoplasms or non-neoplastic conditions characterized by pathological angiogenesis. Non-neoplastic conditions that are amenable to treatment include rheumatoid arthritis, psoriasis, atherosclerosis, diabetic and other proliferative retinopathies including retinopathy of prematurity, retrolental fibroplasia, neovascular glaucoma, age-related macular degeneration, thyroid hyperplasias (including Grave's disease), corneal and other tissue transplantation, chronic inflammation, lung inflammation, nephrotic syndrome, preeclampsia, ascites, pericardial effusion (such as that associated with pericarditis), and pleural effusion.

The antibodies of the invention are preferably used in the treatment of tumors in which angiogenesis plays an important role in tumor growth, including cancers and benign tumors. Examples of cancer to be treated herein include, but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. More particularly, cancers that are amenable to treatment by the antibodies of the invention include breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, melanoma, ovarian cancer, mesothelioma, and multiple myeloma. More preferably, the methods of the invention are used to treat colorectal cancer in a human patient.

The present invention encompasses antiangiogenic therapy, a novel cancer treatment strategy aimed at inhibiting the development of tumor blood vessels required for providing nutrients to support tumor growth. Because angiogenesis is involved in both primary tumor growth and metastasis, the antiangiogenic treatment provided by the invention is capable of inhibiting the neoplastic growth of tumor at the primary site as well as preventing metastasis of tumors at the secondary sites, therefore allowing attack of the tumors by other therapeutics.

Combination Therapies

It is contemplated that when used to treat various diseases such as tumors, the antibodies of the invention can be combined with other therapeutic agents suitable for the same or similar diseases. When used for treating cancer, antibodies of the present invention may be used in combination with conventional cancer therapies, such as surgery, radiotherapy, chemotherapy or combinations thereof.

In certain aspects, other therapeutic agents useful for combination cancer therapy with the antibody of the invention include other anti-angiogenic agents. Many anti-angiogenic agents have been identified and are known in the arts, including those listed by Carmeliet and Jain (2000). Preferably, the anti-VEGF antibody of the invention is used in combination with another VEGF antagonist or a VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof. Alternatively, or in addition, two or more anti-VEGF antibodies may be co-administered to the patient.

In some other aspects, other therapeutic agents useful for combination tumor therapy with the antibody of the invention include antagonist of other factors that are involved in tumor growth, such as EGFR, ErbB2 (also known as Her2) ErbB3, ErbB4, or TNF. Sometimes, it may be beneficial to also administer one or more cytokines to the patient. In a preferred embodiment, the VEGF antibody is co-administered with a growth inhibitory agent. For example, the growth inhibitory agent may be administered first, followed by the VEGF antibody. However, simultaneous administration or administration of the VEGF antibody first is also contemplated. Suitable dosages for the growth inhibitory agent are those presently used and may be lowered due to the combined action (synergy) of the growth inhibitory agent and anti-VEGF antibody.

Chemotherapeutic Agents

In certain aspects, the present invention provides a method of treating cancer, by administering effective amounts of an anti-VEGF antibody and one or more chemotherapeutic agents to a patient susceptible to, or diagnosed with, cancer. A variety of chemotherapeutic agents may be used in the combined treatment methods of the invention. An exemplary and non-limiting list of chemotherapeutic agents contemplated is provided herein under "Definition".

As will be understood by those of ordinary skill in the art, the appropriate doses of chemotherapeutic agents will be generally around those already employed in clinical therapies wherein the chemotherapeutics are administered alone or in combination with other chemotherapeutics. Variation in dosage will likely occur depending on the condition being treated. The physician administering treatment will be able to determine the appropriate dose for the individual subject.

By way of example only, standard chemotherapy treatments for metastatic colorectal cancer are described herein below.

In one preferred embodiment, the methods of the invention are used to treat colorectal cancer including metastatic colorectal cancer. Colorectal cancer is the third most common cause of cancer mortality in the United States. It was estimated that approximately 129,000 new cases of colorectal cancer would be diagnosed and 56,000 deaths would occur due to colorectal cancer in the United States in 1999, Landis et al., Cancer J. Clin. 49:8-31 (1999). Approximately 70% of colorectal cancer patients present with disease that is potentially curable by surgical resection, August et al., Cancer Metastasis Rev 3:303-24 (1984). However, the prognosis for the 30% who present with advanced or metastatic disease and for the 20% who relapse following resection is poor. The median survival for those with metastatic disease is 12-14 months, Advanced Colorectal Cancer Meta-Analysis Project, J Clin Oncol 10:896-903 (1992).

The standard treatment for metastatic colorectal cancer in the United States has been until recently chemotherapy with 5-fluorouracil (5-FU) plus a biochemical modulator of 5-FU, leucovorin, Advanced Colorectal Cancer Meta-Analysis Project, J Clin Oncol 10:896-903 (1992); Moertel *N Engl J Med* 330:1136-42 (1994). The combination of 5-FU/leucovorin provides infrequent, transient shrinkage of colorectal tumors but has not been demonstrated to prolong survival compared with 5-FU alone (Advanced Colorectal Cancer Meta-Analysis Project, *J Clin Oncol* 10:896-903 (1992)), and 5-FU has not been demonstrated to prolong survival compared with an ineffective therapy plus best supportive care, Ansfield et al. *Cancer* 39:34-40 (1977). The lack of a demonstrated survival benefit for 5-FU/leucovorin may be due in part to inadequately sized clinical trials. In a large randomized trial of patients receiving adjuvant chemotherapy for resectable colorectal cancer, 5-FU/leucovorin demonstrated prolonged survival compared with lomustine (MeCCNU), vincristine, and 5-FU (MOF; Wolmark et al. *J Clin Oncol* 11: 1879-87 (1993).

In the United States, 5-FU/leucovorin chemotherapy is commonly administered according to one of two schedules: the Mayo Clinic and Roswell Park regimens. The Mayo Clinic regimen consists of an intensive course of 5-FU plus low-dose leucovorin (425 mg/m 2 5-FU plus 20 mg/m 2 leucovorin administered daily by intravenous [IV] push for 5 days, with courses repeated at 4- to 5-week intervals), Buroker et al. J Clin Oncol 12:14-20 (1994). The Roswell Park regimen consists of weekly 5-FU plus high-dose leucovorin (500-600 mg/m 2 5-FU administered by IV push plus 500 mg/m 2 leucovorin administered as a 2-hour infusion weekly for 6 weeks, with courses repeated every 8 weeks), Petrelli et al., J Clin Oncol 7:1419-26 (1989). Clinical trials comparing the Mayo Clinic and Roswell Park regimens have not demonstrated a difference in efficacy but have been underpowered to do so, Buroker et al., J Clin Oncol 12:14-20 (1994); Poon et al., J Clin Oncol 7:1407-18 (1989). The toxicity profiles of the two regimens are different, with the Mayo Clinic regimen resulting in more leukopenia and stomatitis and the Roswell Park regimen resulting in more frequent diarrhea. Patients with newly diagnosed metastatic colorectal cancer receiving either regimen can expect a median time to disease progression of 4-5 months and a median survival of 12-14 months, Petrelli et al., J Clin Oncol 7:1419-26 (1989); Advanced Colorectal Cancer Meta-Analysis Project, J Clin Oncol 10:896-903 (1992); Buroker et al., J Clin Oncol 12:14-20 (1994); Cocconi et al., J Clin Oncol 16:2943-52 (1998).

Recently, a new first-line therapy for metastatic colorectal cancer has emerged. Two randomized clinical trials, each with approximately 400 patients, evaluated irinotecan in combination with 5-FU/leucovorin, Saltz et al., Proc ASCO 18:233a (1999); Douillard et al., Lancet 355:1041-7 (2000). In both studies, the combination of irinotecan/5-FU/leucovorin demonstrated statistically significant increases in survival (of 2.2 and 3.3 months), time to disease progression and response rates as compared with 5-FU/leucovorin alone. The benefits of irinotecan came at a price of increased toxicity: addition of irinotecan to 5-FU/leucovorin was associated with an increased incidence of National Cancer Institute Common Toxicity Criteria (NCI-CTC) Grade ¾ diarrhea, Grade ¾ vomiting, Grade 4 neutropenia, and asthenia compared with 5-FU/leucovorin alone. There is also evidence showing that single-agent irinotecan prolongs survival in the second-line setting, Cunningham et al., Lancet 352:1413-18 (1998); Rougier et al., Lancet 352:1407-12 (1998). Two randomized studies have demonstrated that irinotecan prolongs survival in patients who have progressed following 5-FU therapy. One study compared irinotecan to best supportive care and showed a 2.8-month prolongation of survival; the other study compared irinotecan with infusional 5-FU and showed a 2.2-month prolongation of survival. The question of whether irinotecan has more effect on survival in the first- or second-line setting has not been studied in a well-controlled fashion.

Dosage and Administration

The antibodies and chemotherapeutic agents of the invention are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

In one embodiment, the treatment of the present invention involves the combined administration of an anti-VEGF antibody and one or more chemotherapeutic agents. The present invention contemplates administration of cocktails of different chemotherapeutic agents. The combined administration includes coadministration, using separate formulations or a single pharmaceutical formulation, and consecutive administration in either order, wherein preferably there is a time period while both (or all) active agents simultaneously exert their biological activities. Preparation and dosing schedules for such chemotherapeutic agents may be used according to manufacturers' instructions or as determined empirically by the skilled practitioner. Preparation and dosing schedules for chemotherapy are also described in Chemotherapy Service Ed., M. C. Perry, Williams & Wilkins, Baltimore, Md. (1992). The chemotherapeutic agent may precede, or follow administration of the antibody or may be given simultaneously therewith.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. In a combination therapy regimen, the compositions of the present invention are administered in a therapeutically effective or synergistic amount. As used herein, a therapeutically effective amount is such that co-administration of anti-VEGF antibody and one or more other therapeutic agents, or administration of a composition of the present invention, results in reduction or inhibition of the targeting disease or condition. A therapeutically synergistic amount is that amount of anti-VEGF antibody and one or more other therapeutic agents necessary to synergistically or significantly reduce or eliminate conditions or symptoms associated with a particular disease.

Depending on the type and severity of the disease, about 1 µg/kg to 50 mg/kg (e.g. 0.1-20 mg/kg) of antibody is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. In a preferred aspect, the antibody of the invention is administered every two to three weeks, at a dose ranged from about 5 mg/kg to about 15 mg/kg. More preferably, such dosing regimen is used in combination with a chemotherapy regimen as the first line therapy for treating metastatic colorectal cancer. In some aspects, the chemotherapy regimen involves the traditional high-dose intermittent administration. In some other aspects, the chemotherapeutic agents are administered using smaller and more frequent doses without scheduled breaks ("metronomic chemotherapy"). The progress of the therapy of the invention is easily monitored by conventional techniques and assays.

Further information about suitable dosages is provided in the Example below.

Efficacy of the Treatment

The main advantage of the treatment of the present invention is the ability of producing marked anti-cancer effects in a human patient without causing significant toxicities or adverse effects, so that the patient benefited from the treatment overall. The efficacy of the treatment of the invention can be measured by various endpoints commonly used in evaluating cancer treatments, including but not limited to, tumor regression, tumor weight or size shrinkage, time to progression, duration of survival, progression free survival, overall response rate, duration of response, and quality of life.

Because the anti-angiogenic agents of the invention target the tumor vasculature and not necessarily the neoplastic cells themselves, they represent a unique class of anticancer drugs, and therefore may require unique measures and definitions of clinical responses to drugs. For example, tumor shrinkage of greater than 50% in a 2-dimensional analysis is the standard cut-off for declaring a response. However, the anti-VEGF antibody of the invention may cause inhibition of metastatic spread without shrinkage of the primary tumor, or may simply exert a tumouristatic effect. Accordingly, novel approaches to determining efficacy of an anti-angiogenic therapy should be employed, including for example, measurement of plasma or urinary markers of angiogenesis and measurement of response through radiological imaging.

In one embodiment, the present invention can be used for increasing the duration of survival of a human patient susceptible to or diagnosed with a cancer. Duration of survival is defined as the time from first administration of the drug to death. In a preferred aspect, the anti-VEGF antibody of the invention is administered to the human patient in combination with one or more chemotherapeutic agents, thereby the duration of survival of the patient is effectively increased as compared to a chemotherapy alone. For example, patient group treated with the anti-VEGF antibody combined with a chemotherapeutic cocktail of at least two, preferably three, chemotherapeutic agents may have a median duration of survival that is at least about 2 months, preferably between about 2 and about 5 months, longer than that of the patient group treated with the same chemotherapeutic cocktail alone, said increase being statistically significant. Duration of survival can also be measured by stratified hazard ratio (HR) of the treatment group versus control group, which represents the risk of death for a patient during the treatment. Preferably, a combination treatment of anti-VEGF antibody and one or more chemotherapeutic agents significantly reduces the risk of death by at least about 30% (i.e., a stratified HR of about 0.70), preferably by at least about 35% (i.e., a stratified HR of about 0.65), when compared to a chemotherapy alone.

In another embodiment, the present invention provides methods for increasing progression free survival of a human patient susceptible to or diagnosed with a cancer. Time to disease progression is defined as the time from administration of the drug until disease progression. In a preferred embodiment, the combination treatment of the invention using anti-VEGF antibody and one or more chemotherapeutic agents significantly increases progression free survival by at least about 2 months, preferably by about 2 to about 5 months, when compared to a treatment with chemotherapy alone.

In yet another embodiment, the treatment of the present invention significantly increases response rate in a group of human patients susceptible to or diagnosed with a cancer who are treated with various therapeutics. Response rate is defined as the percentage of treated patients who responded to the treatment. In one aspect, the combination treatment of the invention using anti-VEGF antibody and one or more chemotherapeutic agents significantly increases response rate in the treated patient group compared to the group treated with chemotherapy alone, said increase having a Chi-square p-value of less than 0.005.

In one aspect, the present invention provides methods for increasing duration of response in a human patient or a group of human patients susceptible to or diagnosed with a cancer. Duration of response is defined as the time from the initial response to disease progression. In a combination treatment of the invention using anti-VEGF antibody and one or more chemotherapeutic agents, a statistically significant increase of at least 2 months in duration of response is obtainable and preferred.

Safety of the Treatment

The present invention provides methods of effectively treating cancers without significant adverse effects to the human patient subject to treatment. The clinical outcomes of the treatment according to the invention are somewhat unexpected, in that several adverse events thought to be associated with anti-angiogenic therapies are not observed during the course of treatments according to the present invention. For example, previous clinical studies suggested that treatment with anti-VEGF antibodies may cause thrombosis (fatal in certain case), hypertension, proteinuria and epistaxis (bleeding). However, combination therapy of the invention using anti-VEGF antibody combined with a chemotherapy cocktail comprising at least two, preferably three, chemotherapeutic agents does not significantly increase incident occurrences of these adverse events, when compared with the chemotherapy alone. Thus, the treatment of the present invention unexpectedly contains side effects at acceptable level, at the same time significantly improve anticancer efficacy.

V. Articles of Manufacture

In another embodiment of the invention, an article of manufacture containing materials useful for the treatment of the disorders described above is provided. The article of manufacture comprises a container, a label and a package insert. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an anti-VEGF antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, and syringes. In addition, the article of manufacture comprises a package inserts with instructions for use, including for example a warning that the composition is not to be used in combination with anthacycline-type chemotherapeutic agent, e.g. doxorubicin, or epirubicin, or instructing the user of the composition to administer the anti-VEGF antibody composition and an antineoplastic composition to a patient.

Deposit of Materials

The following hybridoma cell line has been deposited under the provisions of the Budapest Treaty with the American Type Culture Collection (ATCC), Manassas, Va., USA:

| Antibody Designation | ATCC No. | Deposit Date |
|---|---|---|
| A4.6.1 | ATCC HB-10709 | Mar. 29, 1991 |

The following examples are intended merely to illustrate the practice of the present invention and are not provided by way of limitation. The disclosures of all patent and scientific literatures cited herein are expressly incorporated in their entirety by reference.

VI. Examples

Example 1

Addition of an Anti-VEGF Antibody to Bolus Irinotecan/Fluorouracil/Leucovorin (IFL) in First Line Metastatic Colorectal Cancer A multicenter, Phase III, randomized, active-controlled trial was conducted to evaluate the efficacy and safety of bevacizumab when added to standard first-line chemotherapy used to treat metastatic colorectal cancer. The trial enrolled over 900 patients with histologically confirmed, previously untreated, bi-dimensionally measurable metastatic colorectal cancer.

Methods and Materials

Anti-VEGF Antibody Bevacizumab

The anti-VEGF antibody "Bevacizumab (BV)", also known as "rhuMAb VEGF" or "Avastin™", is a recombinant humanized anti-VEGF monoclonal antibody generated according to Presta et al. (1997) Cancer Res. 57:4593-4599. It comprises mutated human IgG1 framework regions and antigen-binding complementarity-determining regions from the murine anti-hVEGF monoclonal antibody A.4.6.1 that blocks binding of human VEGF to its receptors. U.S. Pat. No. 6,582,959; WO 98/45331. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 daltons and is glycosylated.

Identities of the polypeptide and sites of glycosylation were deduced from the amino acid composition and peptide map. The size and charge characteristics of the molecule and the purity of the clinical lots were demonstrated by sodium dodecyl sulfate-polyacrylamide gel electrophoresis or capillary electrophoresis non-gel sieving, isoelectric focusing, as well as ion-exchange and size-exclusion chromatography. The activity of bevacizumab was quantified by a binding enzyme-linked immunosorbent assay or a kinase receptor assay for recombinant human VEGF.

bevacizumab was produced by recombinant DNA technology, using a genetically engineered Chinese hamster ovary cell line. The protein was purified from the cell culture medium by routine methods of column chromatography and filtration. The final product was tested for quality, identity, safety, purity, potency, strength, and excipient/chemical composition according to U.S. Food and Drug Administration guidelines. The purity of bevacizumab is >95%. bevacizumab is supplied as a clear to slightly opalescent, sterile liquid ready for parenteral administration.

Patient Selection

Eligible patients had histologically confirmed metastatic colorectal carcinoma, with bidimensionally measurable disease. Other inclusion criteria included an age of at least 18 years, an Eastern Cooperative Oncology Group (ECOG) performance status of 0 or 1 (Oken et al. (1982) Am. J. Clin. Oncol. 5:649-55), a life expectancy of more than three months, and written informed consent. Adequate hematologic, hepatic, and renal function (including urinary excretion of no more than 500 mg of protein per day) was also required.

Exclusion criteria included prior chemotherapy or biologic therapy for metastatic disease (adjuvant or radiosensitizing use of fluoropyrimidines with or without leucovorin or levamisole more than 12 months before study entry was permitted), receipt of radiotherapy within 14 days before the initiation of study treatment, major surgery within 28 days before the initiation of study treatment, clinically significant cardiovascular disease, clinically detectable ascites, pregnancy or lactation, regular use of aspirin (more than 325 mg per day) or other nonsteroidal and inflammatory agents, preexisting bleeding diatheses or coagulopathy or the need for full-dose anticoagulation, and known central nervous system metastases.

Study Design

Eligible patients were assigned to treatment with the use of a dynamic randomization algorithm that was designed to achieve overall balance between groups; randomization was stratified according to study center, baseline ECOG performance status (0 vs. 1), site of primary disease (colon vs. rectum), and number of metastatic sites (one vs. more than one). Initially, patients were randomly assigned in a 1:1:1 ratio to receive IFL plus placebo, IFL plus bevacizumab, or fluorouracil and leucovorin plus bevacizumab (Table 1), each of which was to continue until disease progression or unacceptable adverse effects occurred or for a maximum of 96 weeks.

TABLE 1

First-Line Treatment Regimens*

| Treatment | Starting Dose | Schedule |
|---|---|---|
| Irinotecan | 125 mg/m² of body-surface area | Once weekly for 4 wk; cycle repeated every 6 wk |
| Fluorouracil | 500 mg/m² | |
| Leucovorin | 20 mg/m² | |
| Placebo | | Every 2 wk |
| Irinotecan | 125 mg/m² | Once weekly for 4 wk; cycle repeated every 6 wk |
| Fluorouracil | 500 mg/m² | |
| Leucovorin | 20 mg/m² | |
| Bevacizumab | 5 mg/kg of body weight | Every 2 wk |
| Fluorouracil | 500 mg/m² | Once weekly for 4 wk; cycle repeated every 8 wk |
| Leucovorin | 500 mg/m² | |
| Bevacizumab | 5 mg/kg | Every 2 wk |

*Treatment with fluorouracil, leucovorin, and bevacizumab was discontinued after the safety of adding bevacizumab to the regimen of irinotecan, fluorouracil, and leucovorin was confirmed. Confirmation occurred after the randomization of 313 patients. All drugs were given intravenously.

An interim analysis was scheduled to be performed after 300 patients underwent randomization, at which time an unblinded, independent data-monitoring committee was to assess the safety of IFL plus bevacizumab, on the basis of all the available safety information, including the number of deaths in each group, but in the absence of information related to tumor response. If the data-monitoring committee found no untoward adverse events attributable to the addition of bevacizumab to IFL, the enrollment of patients in the group assigned to receive fluorouracil and leucovorin plus bevacizumab was to be discontinued, and additional patients would be randomly assigned in a 1:1 ratio to receive either IFL plus placebo or IFL plus bevacizumab. However, if the data-monitoring committee concluded that the safety profile of IFL plus bevacizumab was unacceptable, assignment to that treatment was to be discontinued, and patients would instead be randomly assigned in a 1:1 ratio to receive either the combination of fluorouracil and leucovorin plus bevacizumab or IFL plus placebo.

Tumor responses and progression were determined with the use of the Response Evaluation Criteria in Solid Tumors. Therasse et al. (2000) *J. Natl. Cancer Inst.* 92:205-16. At the time of disease progression, the treatment assignment was revealed and patients could be offered second-line treatment. Such patients in the group assigned to bevacizumab-containing treatment had the option to continue bevacizumab during this second-line treatment. No crossovers were allowed in the group given IFL plus placebo. Patients assigned to a treatment containing bevacizumab who had no signs of progressive disease at the end of the 96-week study period could continue to receive bevacizumab in a separate extension study. Patients in a group receiving bevacizumab who had a confirmed complete response or unacceptable adverse effects from chemotherapy could discontinue chemotherapy and receive bevacizumab alone.

Bevacizumab (or placebo) was administered concomitantly with chemotherapy. Doses of bevacizumab and chemotherapy were recalculated if a patient's weight changed by at least 10 percent during the study. Standard intracycle and intercycle dose modifications of irinotecan and fluorouracil (according to the package insert) were permitted in patients with treatment-related adverse events. The doses of leucovorin and bevacizumab were not altered.

In the analysis of survival and subsequent treatment, all patients were followed until death, loss to follow-up, or termination of the study.

Assessments

After the baseline evaluation, tumor status was assessed every 6 weeks for the first 24 weeks of the study and then every 12 weeks for the remainder of therapy. All complete and partial responses required confirmation at least four weeks after they were first noted.

Safety was assessed on the basis of reports of adverse events, laboratory-test results, and vital sign measurements. Adverse events were categorized according to the Common Toxicity Criteria of the National Cancer Institute, version 2, in which a grade of 1 indicates mild adverse events, a grade of 2 moderate adverse events, a grade of 3 serious adverse events, and a grade of 4 life-threatening adverse events. Prespecified safety measures included the incidence of all adverse events, all serious adverse events, and adverse events that have been associated with bevacizumab—hypertension, thrombosis, bleeding of grade 3 or 4, and proteinuria—as well as diarrhea of grade 3 or 4, and changes from baseline in various laboratory values and vital signs.

To monitor the safety of the regimen of IFL plus placebo and of IFL plus bevacizumab, the incidence of death, serious adverse events, diarrhea of grade 3 or 4, bleeding of grade 3 or 4 from any source, and thrombosis was monitored during the study in an un-blinded fashion by the data-safety monitoring committee until the completion of recruitment or the time of the interim analysis of efficacy, whichever came first.

Statistical Analysis

The primary outcome measure was the duration of overall survival; survival was measured without regard to subsequent treatments. There was no crossover between groups, however. Survival analysis techniques such as the Kaplan-Meier method, log-rank test, and Cox proportional hazards model were used. Secondary outcome measures were progression-free survival, objective response rates (complete and partial responses), the duration of responses, and the quality of life.

For patients who were alive at the time of analysis, data on survival were censored at the time of the last contact. Progression-free survival was defined as the time from randomization to progression or death during the study, with death during the study defined as any death that occurred within 30 days after the last dose of bevacizumab or chemotherapy. For patients without disease progression at the time of the final analysis, data on progression-free survival were censored at the last assessment of tumor status or on day 0 if no further assessment was performed after baseline. Patients without adequate follow-up data were categorized as having no response.

To detect a hazard ratio of 0.75 for death in the group given IFL plus bevacizumab as compared with the control group, approximately 385 deaths were required. All calculations were performed with the log-rank test and involved two-sided P values, with an alpha value of 0.05, a statistical power of 80 percent, and one interim analysis of efficacy.

Interim analyses were conducted in an un-blinded fashion. An interim analysis of safety was conducted after the random assignment of approximately 100 patients to each group. A second interim analysis of safety and efficacy was performed after 193 deaths had occurred (half the number of required events).

Efficacy analyses were performed according to the intention-to-treat principle. Safety analyses included all patients who received at least one dose of study medication.

Results

Characteristics of the Patients

During a period of about twenty months, 923 patients underwent randomization at 164 sites in the United States, Australia, and New Zealand. After 313 patients had been randomly assigned to one of the three groups—100 to IFL plus placebo, 103 to IFL plus bevacizumab, and 110 to fluorouracil, leucovorin, and bevacizumab—assignment to the group given fluorouracil, leucovorin, and bevacizumab was halted (the results in this group are not reported). This step was required by the protocol after the first formal interim analysis of safety concluded that the regimen of IFL plus bevacizumab had an acceptable safety profile and that assignment to this group could continue.

The intention-to-treat analysis of the primary end point of overall survival included 411 patients in the group given IFL plus placebo and 402 patients in the group given IFL plus bevacizumab. Table 2 shows selected demographic and baseline characteristics, which were well balanced between the groups. Similar numbers of patients in each group had previously undergone surgery or received radiation therapy or adjuvant chemotherapy for colorectal cancer.

Treatment

The median duration of therapy was 27.6 weeks in the group given IFL plus placebo and 40.4 weeks in the group given IFL plus bevacizumab. The percentage of the planned dose of irinotecan that was given was similar in the two groups (78 percent in the group given IFL plus placebo and 73 percent in the group given IFL plus bevacizumab).

As of the date of data cutoff, 33 patients in the group given IFL plus placebo and 71 in the group given IFL plus bevacizumab were still taking their assigned initial therapy. The rates of use of second-line therapies that may have affected survival, such as oxaliplatin or metastasectomy, were well balanced between the two groups. In both groups, approximately 50 percent of patients received some form of second line therapy; 25 percent of all patients received oxaliplatin, and less than 2 percent of patients underwent metastasectomy.

TABLE 2

Selected Demographic and Baseline Characteristics.*

| Characteristic | IFL plus Placebo (N = 411) | IFL plus Bevacizumab (N = 402) |
|---|---|---|
| Sex (%) | | |
| MALE | 60 | 59 |
| FEMALE | 40 | 41 |
| MEAN AGE (YR) | 59.2 | 59.5 |
| Race (%) | | |
| White | 80 | 79 |
| Black | 11 | 12 |
| Other | 9 | 9 |
| Location of center (%) | | |
| United States | 99 | 99 |
| Australia or New Zealand | <1 | <1 |
| ECOG performance status (%) | | |
| 0 | 55 | 58 |
| 1 | 44 | 41 |
| 2 | <1 | <1 |
| Type of cancer (%) | | |
| Colon | 81 | 77 |
| Rectal | 19 | 23 |
| Number of metastatic sites (%) | | |
| 1 | 39 | 37 |
| >1 | 61 | 63 |
| Prior cancer therapy (%) | | |
| Adjuvant chemotherapy | 28 | 24 |
| Radiation therapy | 14 | 15 |
| Median duration of metastatic disease (mo) | 4 | 4 |

*There were no significant differences between groups. IFL denotes irinotecan, fluorouracil, and leucovorin, and ECOG Eastern Cooperative Oncology Group.

Efficacy

The median duration of overall survival, the primary end point, was significantly longer in the group given IFL plus bevacizumab than in the group given IFL plus placebo (20.3 months vs. 15.6 months), which corresponds to a hazard ratio for death of 0.66 (P<0.001) (Table 3 and FIG. 1), or a reduction of 34 percent in the risk of death in the bevacizumab group. The one-year survival rate was 74.3 percent in the group given IFL plus bevacizumab and 63.4 percent in the group given IFL plus placebo (P<0.001). In the subgroup of patients who received second-line treatment with oxaliplatin, the median duration of overall survival was 25.1 months in the group given IFL plus bevacizumab and 22.2 months in the group given IFL plus placebo.

Figure 2:
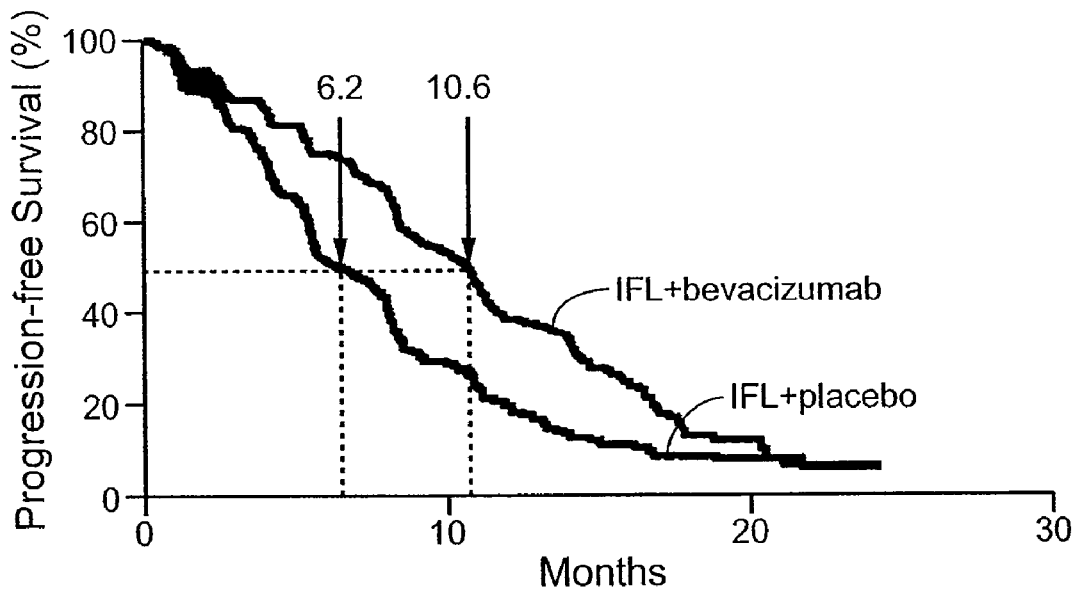
FIG. 2 represents Kaplan-Meier estimates of progression-free survival. The median duration of progression-free survival (indicated by the dotted lines) was 10.6 months in the group given irinotecan, fluorouracil, and leucovorin (IFL) plus bevacizumab, as compared with 6.2 months in the group given IFL plus placebo, corresponding to a hazard ratio for progression of 0.54 (P<0.001).
Figure 3A:
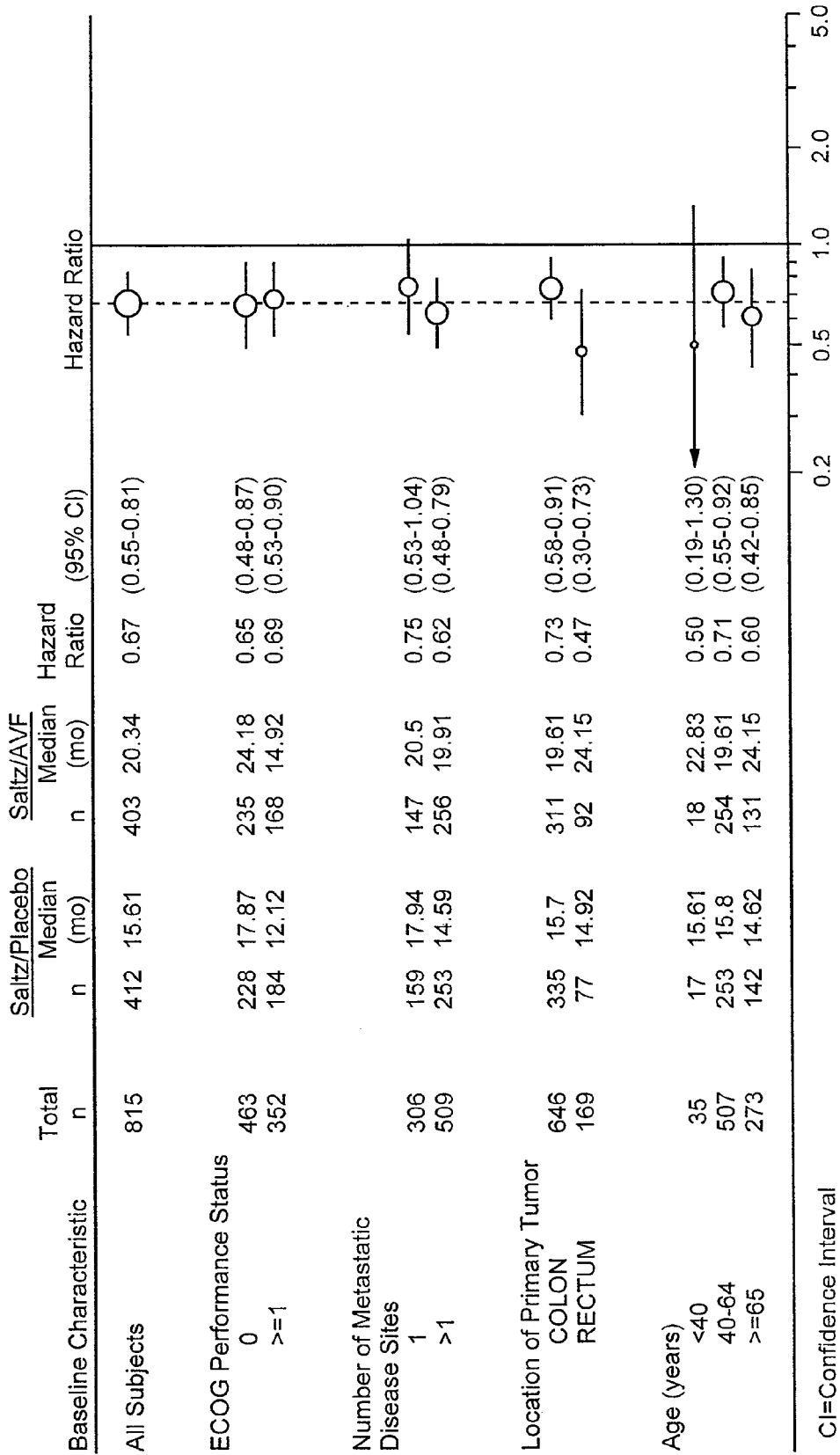
FIGS. 3A-3C provide analysis of duration of survival by different subgroups of patients divided by baseline characteristics.
Figure 3B:
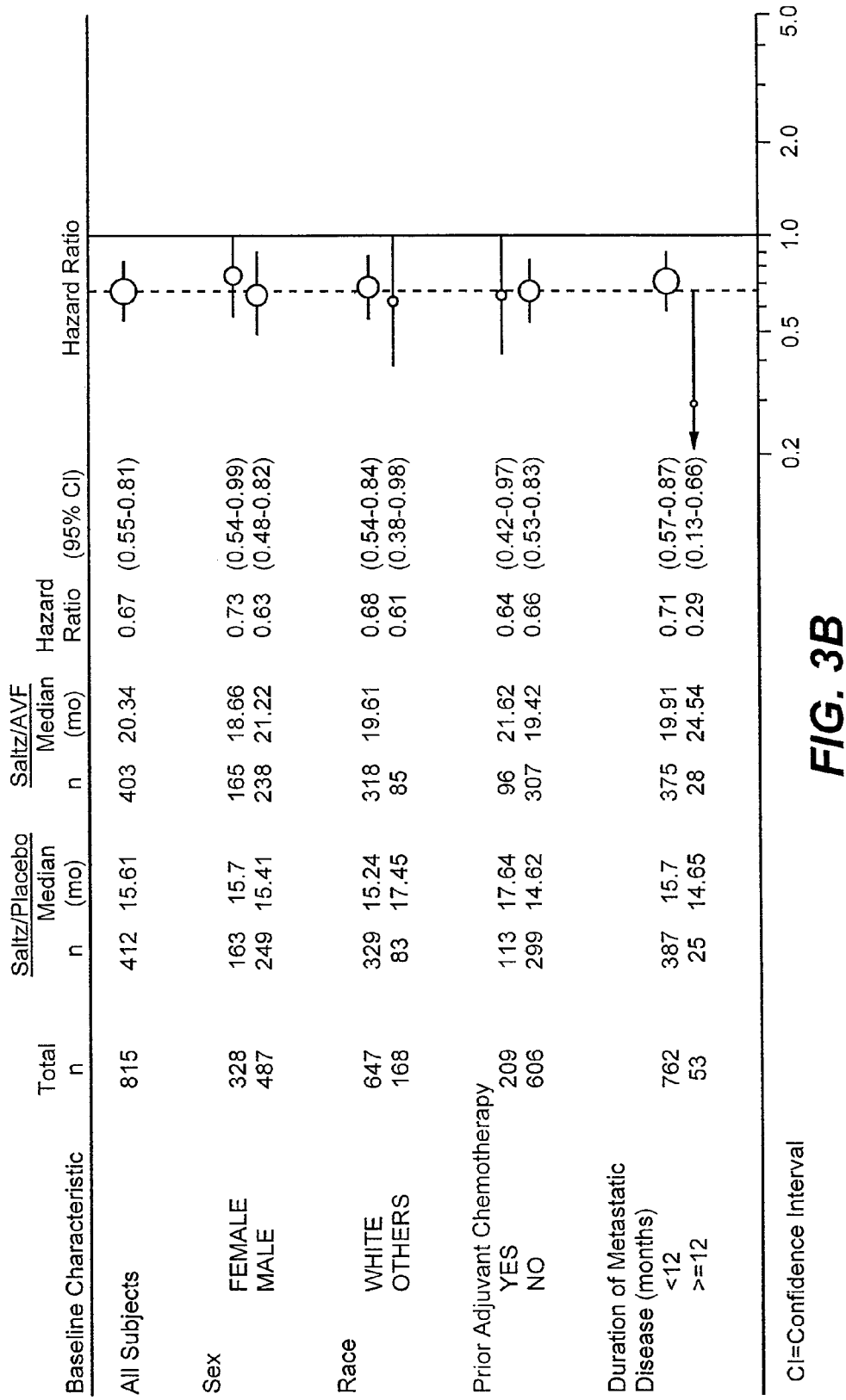
Figure 3C:
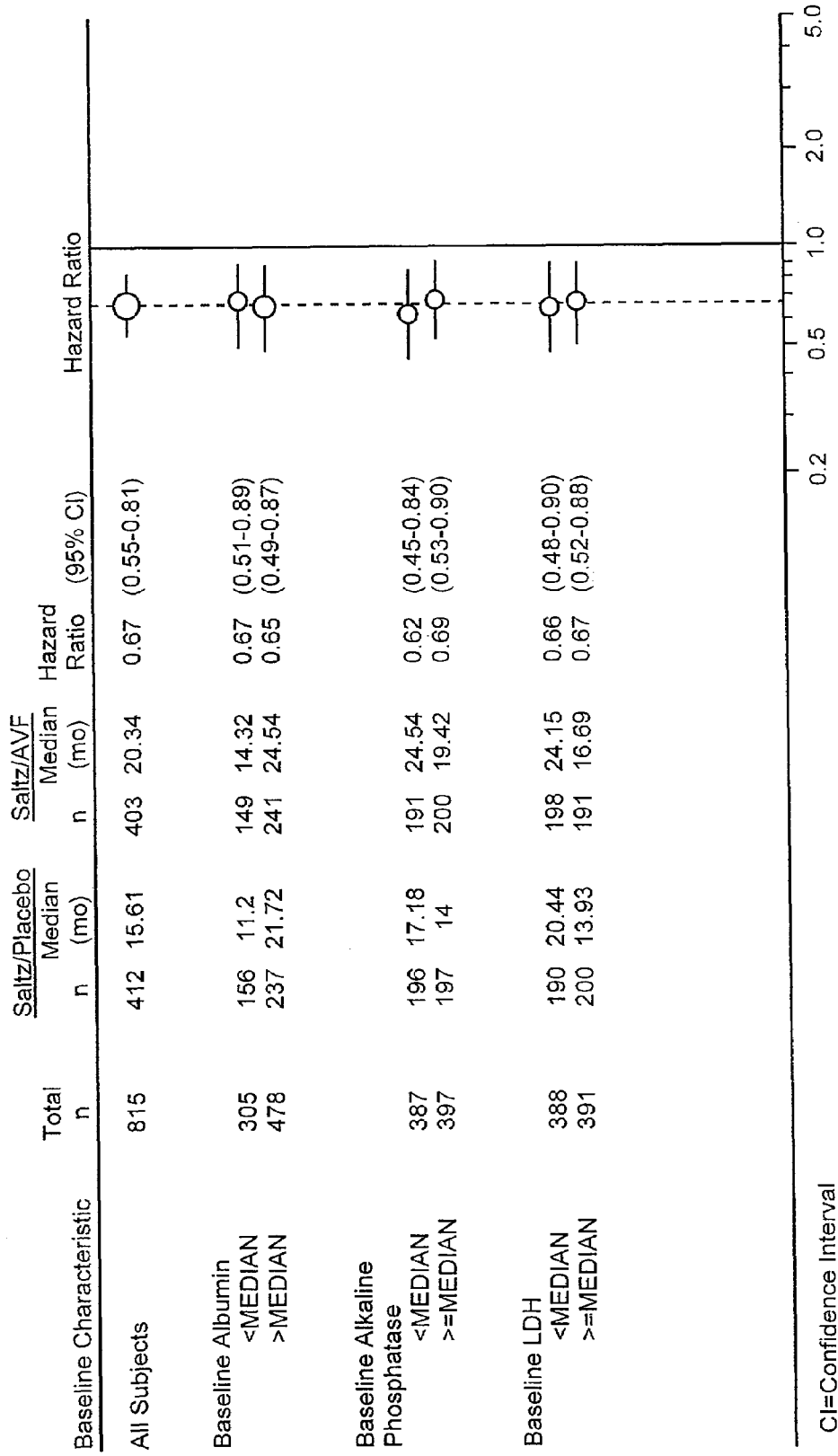

The addition of bevacizumab to IFL was associated with increases in the median duration of progression-free survival (10.6 months vs. 6.2 months; hazard ratio for progression, 0.54, for the comparison with the group given IFL plus placebo; P<0.001); response rate (44.8 percent vs. 34.8 percent; P=0.004); and the median duration of response (10.4 months vs. 7.1 months; hazard ratio for progression, 0.62; P=0.001) (Table 3). FIG. 2 shows the Kaplan-Meier estimates of progression free survival. Treatment effects were consistent across prespecified subgroups, including those defined according to age, sex, race, ECOG performance status, location of the primary tumor, presence or absence of prior adjuvant therapy, duration of metastatic disease, number of metastatic sites, years since the diagnosis of colorectal cancer, presence or absence of prior radiotherapy, baseline tumor burden, and serum concentrations of albumin, alkaline phosphatase, and lactate dehydrogenase.

TABLE 3

Analysis of Efficacy*

| End Point | IFL plus Placebo | IFL plus Bevacizumab | P Value |
|---|---|---|---|
| Median survival (mo) | 15.6 | 20.3 | <0.001 |
| Hazard ratio for death | | 0.66 | |
| One-year survival rate (%) | 63.4 | 74.3 | <0.001 |
| Progression-free survival (mo) | 6.2 | 10.6 | <0.001 |
| Hazard ratio for progression | | 0.54 | |
| Overall response rate (%) | 34.8 | 44.8 | 0.004 |
| Complete response | 2.2 | 3.7 | |
| Partial response | 32.6 | 41.0 | |
| Median duration of response (mo) | 7.1 | 10.4 | 0.001 |
| Hazard ratio for relapse | | 0.62 | |

*IFL denotes irinotecan, fluorouracil, and leucovorin.

Safety

Table 4 presents the incidence of selected grade 3 or 4 adverse events during the assigned treatment, without adjustment for the median duration of therapy (27.6 weeks in the group given IFL plus placebo and 40.4 weeks in the group given IFL plus bevacizumab). The incidence of any grade 3 or 4 adverse events was approximately 10 percentage points higher among patients receiving IFL plus bevacizumab than among patients receiving IFL plus placebo, largely because of an increase in the incidence of grade 3 hypertension (requiring treatment) and small increases in the incidence of grade 4 diarrhea and leukopenia. However, there was no significant difference in the incidence of adverse events leading to hospitalization or to the discontinuation of study treatment or in the 60-day rate of death from any cause.

TABLE 4

Selected Adverse Events.*

| Adverse Event | IFL plus Placebo (N = 397) percent | IFL plus Bevacizumab (N = 393) percent |
|---|---|---|
| Any grade 3 or 4 adverse event | 74.0 | 84.9** |
| Adverse event leading to hospitalization | 39.6 | 44.9 |
| Adverse event leading to discontinuation of treatment | 7.1 | 8.4 |
| Adverse event leading to death | 2.8 | 2.6 |
| Death within 60 days | 4.9 | 3.0 |
| Grade 3 or 4 leukopenia | 31.1 | 37.0 |
| Hypertension | | |
| Any | 8.3 | 22.4** |
| Grade 3 | 2.3 | 11.0** |
| Any thrombotic event | 16.2 | 19.4 |
| Deep thrombophletitis | 6.3 | 8.9 |
| Pulmonary embolus | 5.1 | 3.6 |
| Grade 3 or 4 bleeding | 2.5 | 3.1 |
| Proteinuria | | |
| Any | 21.7 | 26.5 |
| Grade 2 | 5.8 | 3.1 |
| Grade 3 | 0.8 | 0.8 |
| Gastrointestinal perforation | 0.0 | 1.5 |

*Data were not adjusted for differences in the median duration of therapy between the group given irinotecan, fluorouracil, and leucovorin (IFL) plus placebo and the group given IFL plus bevacizumab (27.6 weeks vs. 40.4 weeks).
**P < 0.01. Only patients who received at least one study-drug treatment are included.

Phase 1 and 2 trials had identified hemorrhage, thromboembolism, proteinuria, and hypertension as possible bevacizumab-associated adverse effects. However, in the present study, only the incidence of hypertension was clearly increased in the group given IFL plus bevacizumab, as compared with the group given IFL plus placebo. All episodes of hypertension were manageable with standard oral antihypertensive agents (e.g., calcium-channel blockers, angiotensin-converting-enzyme inhibitors, and diuretics). There were no discontinuations of bevacizumab therapy, hypertensive crises, or deaths related to hypertension in the bevacizumab group.

Rates of grade 2 or 3 proteinuria (there were no episodes of grade 4 proteinuria or nephrotic syndrome) and grade 3 or 4 bleeding from any cause were similar in the two groups, although all three cases of grade 4 bleeding were in the group given IFL plus bevacizumab. The incidence of all venous and arterial thrombotic events was 19.4 percent in the group given IFL plus bevacizumab and 16.2 percent in the group given IFL plus placebo (P=0.26).

Gastrointestinal perforation occurred in six patients (1.5 percent) receiving IFL plus bevacizumab. One patient died as a direct result of this event, whereas the other five recovered (three of them were able to restart treatment without subsequent complications). Of the six patients with a perforation, three had a confirmed complete or partial response to IFL plus bevacizumab. Factors other than the study treatment that may have been associated with gastrointestinal perforation were colon surgery within the previous two months in two patients and peptic-ulcer disease in one patient.

The results of this phase III study provide direct support for a broadly applicable use of antiangiogenic agents in the treatment of cancer. The addition of bevacizumab, an anti-VEGF antibody, to IFL chemotherapy conferred a clinically meaningful and statistically significant improvement in cancer patients as measured by, for example, overall survival, progression-free survival, response rate and duration of response. The increase of 4.7 months in the median duration of survival attributable to bevacizumab is as large as or larger than that observed in any other phase 3 trial for the treatment of colorectal cancer. Goldberg et al. (2004) J. Clin. Oncol. 22:23-30. The median survival of 20.3 months in the bevacizumab-treated population occurred in spite of the limited availability of oxaliplatin for second-line therapy during this trial.

As compared with IFL alone, the regimen of IFL plus bevacizumab increased progression-free survival from a median of 6.2 months to 10.6 months, the overall response rate from 34.8 percent to 44.8 percent, and the median duration of response from 7.1 months to 10.4 months. These improvements are clinically meaningful. It was not predicted that the absolute improvement in the response rate of 10 percent with IFL plus bevacizumab would have been associated with an increase in survival of this magnitude. This observation suggests that the primary mechanism of bevacizumab is the inhibition of tumor growth, rather than cytoreduction.

This clinical benefit was accompanied by a relatively modest increase in side effects of treatment, which were easily managed. There was an absolute increase of approximately 10 percent in the overall incidence of grade 3 and 4 adverse effects, attributable largely to hypertension requiring treatment, diarrhea, and leukopenia. The 60-day rates of death from any cause, hospitalization, and discontinuation of treatment were not significantly increased by the addition of bevacizumab to IFL.

Previous phase 1 and 2 clinical trials suggested that treatment with bevacizumab alone or with chemotherapy resulted in an increased incidence of thrombosis, bleeding, proteinuria, and hypertension. Kabbinavar et al. (2003) J. Clin.

*Oncol.* 21:60-65; Yang et al. (2003) *New Engl. J. Med.* 349: 427-34. With the exception of hypertension, an excess of these side effects was not found as compared with their incidence in the group given IFL plus placebo—thus highlighting the importance of randomized, placebo-controlled studies for the evaluation of safety as well as efficacy. One new potential adverse effect that occurred was gastrointestinal perforation. This complication was uncommon and had variable clinical presentations. Severe bowel complications, particularly in patients with neutropenia, have been reported with IFL and other chemotherapy regimens for colorectal cancer and in one series, fistulas were reported in over 2 percent of patients treated with fluorouracil-based regimens. Saltz et al. (2000) *New Engl. J. Med.* 343:905-914; Rothenberg et al. (2001) *J. Clin. Oncol.* 19:3801-7; Tebbutt et al. (2003) *Gut* 52:568-73. No such events occurred in the group given IFL plus placebo, whereas six cases were observed in the group given IFL plus bevacizumab (1.5 percent), sometimes in the setting of overall tumor responses. Although three of these six patients were able to restart treatment without subsequent complications, one patient died and two discontinued therapy permanently as a result of this complication.

While previous animal studies and early phase clinical trials have suggested uses of anti-angiogenic therapy for treating cancer, the present study showed for the first time that using an angiogenic inhibitor, such as an anti-VEGF antibody, indeed results in statistically significant and clinically meaningful benefits for cancer patients.

Example 2

Addition of Bevacizumab to Bolus 5-FU/Leucovorin in First-Line Metastatic Colorectal Cancer This randomized, phase II trial compared bevacizumab plus 5-fluorouracil and leucovorin (5-FU/LV) versus placebo plus 5-FU/LV as first-line therapy in patients considered nonoptimal candidates for first-line irinotecan.

Patients and Methods

Patient Eligibility

Patients with histologically confirmed, previously untreated, measurable metastatic colorectal cancer were eligible if, in the judgment of the investigator, they were not optimal candidates for first-line irinotecan-containing therapy and had at least one of the following characteristics: age above 65 years, ECOG PS of 1 or 2, serum albumin equal or less than 3.5 g/dL, or prior radiotherapy to abdomen or pelvis. Patients were excluded if they had undergone major surgical procedures or open biopsy, or had experienced significant traumatic injury, within 28 days prior to study entry; anticipated need for major surgery during the course of the study; were currently using or had recently used therapeutic anticoagulants (except as required for catheter patency), thrombolytic therapy or chronic, daily treatment with aspirin ($\geq$325 mg/day) or nonsteroidal anti-inflammatory medications; had a serious, non-healing wound, ulcer, or bone fracture; had a history or evidence of CNS metastases; were pregnant or lactating; or had proteinuria or clinically significant impairment of renal function at baseline. All patients provided written informed consent for their participation.

Study Design and Treatments

An interactive voice response system was used to randomly assign eligible patients to one of two treatment groups: 5-FU/LV plus placebo or 5-FU/LV plus bevacizumab. A dynamic randomization algorithm was utilized to achieve balance overall and within each of the following categories: study center, baseline ECOG performance status (0 vs.$\geq$1), site of primary disease (colon vs. rectum), and number of metastatic sites (1 vs.>1). The 5-FU/LV treatment, comprising LV 500 mg/m$^2$ over 2 hours and 5-FU 500 mg/m$^2$ as a bolus midway through the LV infusion (Roswell Park regimen; Petrelli et al. (1989) *J. Clin. Oncol.* 7:1419-1426), was administered weekly for the first 6 weeks of each 8-week cycle. Chemotherapy was continued until study completion (96 weeks) or disease progression. Bevacizumab 5 mg/kg or placebo was administered every 2 weeks. Patients in the bevacizumab arm who had a confirmed complete response or experienced unacceptable toxicity as a result of chemotherapy treatment were allowed to discontinue 5-FU/LV and continue receiving bevacizumab alone as first-line treatment. At the time of disease progression, patients were unblinded to their treatment assignment and could receive any second-line treatment at the discretion of the investigator. Only patients who had been randomized to the bevacizumab group could receive bevacizumab as a component of second-line treatment. After completing the study, patients were followed for any subsequent treatment and survival every 4 months until death, loss to follow-up, or termination of the study.

Study Assessments

Patients underwent an assessment of tumor status at baseline and at completion of every 8-week cycle using appropriate radiographic techniques, typically spiral CT scanning. Tumor response, or progression, was determined by both the investigator and an independent radiology facility (IRF) utilizing the Response Evaluation Criteria in Solid Tumors. Therasse et al. (2000). The IRF assessment was performed without knowledge of the treatment assignment or investigator assessment. In addition, patients completed the Functional Assessment of Cancer Therapy—Colorectal (FACT-C), Version 4, a validated instrument for assessing quality of life (QOL) in colorectal cancer patients, at baseline and prior to each treatment cycle until disease progression. Ward et al. (1999) *Qual. Life Res.* 8: 181-195.

Safety was assessed from reports of adverse events, laboratory test results, and vital sign measurements. Adverse events and abnormal laboratory results were categorized using the National Cancer Institute Common Toxicity Criteria (NCI-CTC), Version 2. Prespecified safety measures included four adverse events of special interest (hypertension, proteinuria, thrombosis, and bleeding) based on findings of previous clinical trials of bevacizumab.

Statistical Analysis

The primary outcome measure was duration of overall survival. Secondary outcome measures included progression-free survival, objective response rate (complete and partial), response duration, and change in the FACT-C QOL score. Survival duration was defined as the time from randomization to death. For patients alive at the time of analysis, duration of survival was censored at the date of last contact. Progression-free survival was defined as the time from randomization to the earlier of disease progression or death on study, defined as death from any cause within 30 days of the last dose of study drug or chemotherapy. For patients alive without disease progression at the time of analysis, progression-free survival was censored at their last tumor assessment, or day 1 (the first day of study treatment) if no postbaseline assessment was performed. In the analysis of objective response, patients without tumor assessments were categorized as nonresponders. Disease progression and response analyses were based on the IRF assessments. Change in quality of life was analyzed as time to deterioration in QOL (TDQ), defined as the length of time from randomization to a the earliest of a ≧3-point decrease from baseline in colon-cancer specific FACT-C subscale score (CCS), disease progression, or death on study. TDQ was also determined for the TOI-C (sum of CCS, physical and functional well-being) and total FACT-C for changes from baseline of 7 and 9 points, respectively.

To detect a hazard ratio of 0.61 for death in the 5-FU/LV/bevacizumab group relative to the 5-FU/LV/placebo group, approximately 133 deaths were required. A two-tailed, log-rank test at the 0.05 level of significance with 80% power and two interim analyses were assumed in the calculations. Interim analyses were conducted by an unblinded, independent Data Monitoring Committee (DMC). A safety interim analysis was conducted after 44 deaths and a second safety and efficacy interim analysis was conducted after 89 deaths. The interim efficacy analysis was governed by a formal group sequential stopping rule based on an O'Brien-Fleming spending function. Kaplan-Meier methodology was applied to estimate the median survival, progression free survival, and duration of response time for each treatment group. Hazard ratios for the bevacizumab group relative to the placebo group were determined using the stratified Cox proportional hazards model. A two-sided stratified log rank test was used to compare the two groups. Stratified analyses included baseline ECOG performance status, site of primary disease, and the number of metastatic sites. Objective response rates were compared by the Chi-squared test. As exploratory analyses, the Cox proportional hazards model was used to estimate the effect of risk factors on modifications of treatment effect for duration of survival and progression-free survival. Efficacy analyses were performed on the intent-to-treat population, defined as all randomized patients. Safety analyses included all patients who received at least one dose of study drug.

Results

Patient Characteristics

In a period of twenty three months, 209 patients were randomized at 60 sites in the United States and Australia/New Zealand. For the intent-to-treat analysis of the primary endpoint (overall survival), there were 105 patients in the 5-FU/LV/placebo group and 104 in the 5-FU/LV/bevacizumab group. Selected demographic and baseline characteristics similar to those described in Example 1 were reasonably balanced between treatment groups. Low serum albumin (≦3.5 g/dL) at baseline was less common in the bevacizumab group than in the placebo group.

Treatment

The median duration of therapy was 23 weeks in the 5-FU/LV/placebo group and 31 weeks in the 5-FU/LV/bevacizumab group, and the 5-FU dose intensity (percentage of planned 5-FU doses actually received) in the two groups was similar (92% vs. 84%) during the treatment course. As of the date of date cut-off, 1 patient in the 5-FU/LV/placebo group and 7 in the 5-FU/LV/bevacizumab group remained on the assigned initial therapy. Subsequent therapies, which may have influenced survival, were used in approximately 50% of patients in both groups, although more patients in the 5-FU/LV/placebo group were treated with the active agents irinotecan and oxaliplatin.

Efficacy

Figure 4:
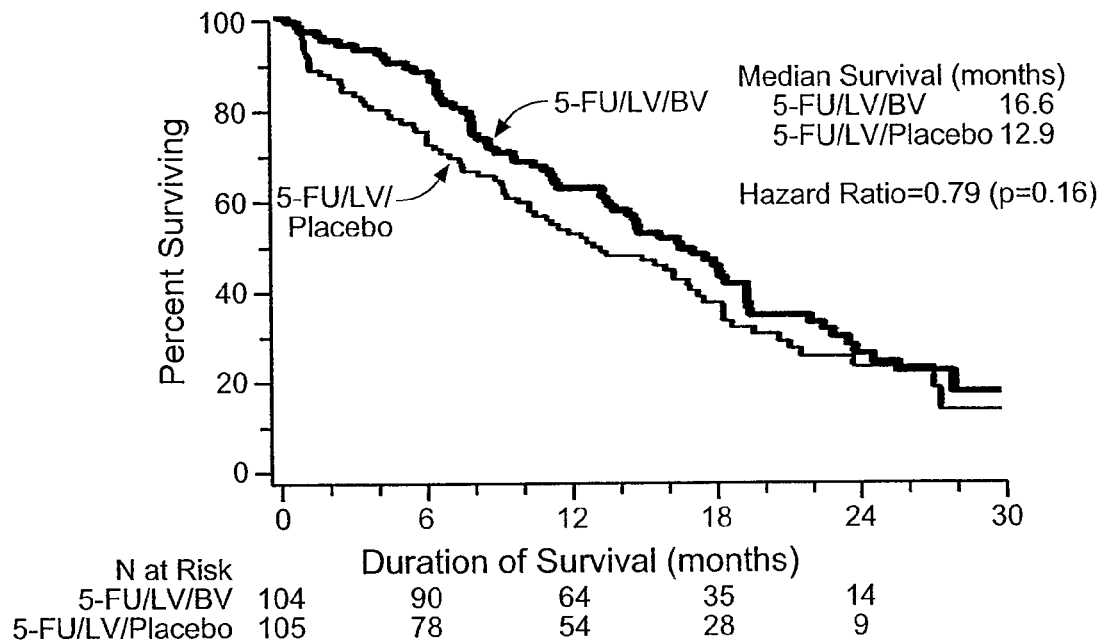
FIG. 4 represents Kaplan-Meier estimates of survival comparing the group given 5-FU/LV plus placebo vs. the group given 5-FU/LV plus bevacizumab (BV).
Figure 5:
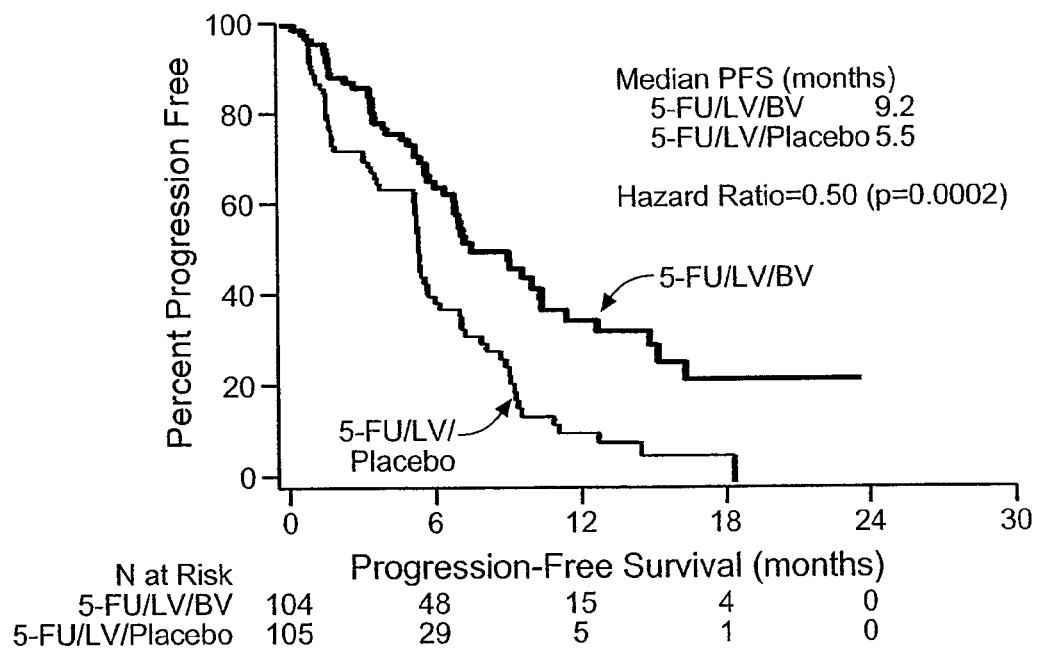
FIG. 5 represents Kaplan-Meier estimates of progression-free survival comparing the group given 5-FU/LV plus placebo vs. the group given 5-FU/LV plus bevacizumab (BV).

Overall survival, the primary endpoint, was longer in the 5-FU/LV/bevacizumab group (median, 16.6 months) than in the 5-FU/LV/placebo group (median, 12.9 months), demonstrating a trend toward significance. The hazard ratio of death was estimated to be 0.79 (95% CI, 0.56 to 1.10; P=0.16; Table 5 and FIG. 4). The addition of bevacizumab to 5-FU/LV was associated with increases in median progression-free survival (9.2 vs. 5.5 months; hazard ratio=0.50; 95% CI, 0.34 to 0.73; P=0.0002, Table 5 and FIG. 4), response rate (26.0% vs. 15.2%, P=0.055), and median duration of response (9.2 months vs. 6.8 months; hazard ratio=0.42; 95% CI, 0.15 to 1.17; P=0.088). A further analysis of treatment effect on overall survival by baseline characteristics showed that patients with low serum albumin (≦3.5 g/dL) at baseline appeared to derive a significant survival benefit (hazard ratio=0.46; 95% CI, 0.29 to 0.74; P=0.001).

TABLE 5

Summary of Efficacy Analysis

| Efficacy Parameter | 5-FU/LV/ Placebo (N = 105) | 5-FU/LV/ Bevacizumab (N = 104) | P-value |
|---|---|---|---|
| Median survival (months) | 12.9 | 16.6 | |
| Hazard ratio | | 0.79 | 0.160 |
| 95% CI | | 0.56 to 1.10 | |
| Progression-free survival (months) | 5.5 | 9.2 | |
| Hazard ratio | | 0.50 | 0.0002 |
| 95% CI | | 0.34 to 0.73 | |
| Overall response rate (%) | 15.2 | 26.0 | 0.055 |
| Complete response | 0 | 0 | |
| Partial response | 15.2 | 26.0 | |
| Duration of response (months) | 6.8 | 9.2 | |
| Hazard ratio | | 0.42 | 0.088 |
| 95% CI | | 0.15 to 1.17 | |

5-FU/LV = 5 fluorouracil/leucovorin

Bevacizumab treatment had no detrimental effect on quality of life, and the TDQ results suggest a possible beneficial effect. The median TDQ as measured by the CCS score was 3.0 months in the 5-FU/LV/placebo group and 3.1 months in the 5-FU/LV/bevacizumab group (hazard ratio=0.79, P=0.188). The median TDQ for placebo-treated and bevacizumab-treated patients as measured by secondary TDQ measures was 2.3 and 3.2 months (TOI-C; hazard ratio=0.71, P=0.048) and 2.6 and 3.6 months (total FACT-C; hazard ratio=0.66, P=0.016).

Safety

A total of 204 patients (104 5-FU/LV/placebo and 100 5-FU/LV/bevacizumab) who received at least one dose of study drug comprised the safety population. A 16% increase (71% versus 87%) in total grade 3 and 4 toxicities was observed for patients receiving bevacizumab. Adverse events leading to death or study discontinuation were similar in the two groups, as were adverse events known to be associated with 5-FU/LV (specifically, diarrhea and leukopenia). Two patients, both in the 5-FU/LV/bevacizumab group, experienced a bowel perforation event. These events occurred at day 110 and day 338 of treatment, and both were determined to be associated with a colonic diverticulum at surgical exploration. One patient died as a result of this complication. Previous clinical trials had suggested hemorrhage, thromboembolism, proteinuria, and hypertension as possible bevacizumab-associated toxicities; however, in this study, no increases were seen in venous thrombosis, ≧grade 3 bleeding, or clinically significant (≧grade 3) proteinuria. Arterial thrombotic events (myocardial infarction, stroke, or peripheral arterial thrombotic event) occurred in 10 patients in the 5-FU/LV/bevacizumab group, compared to 5 patients in the 5-FU/LV/placebo group.

The 5-FU/LV/placebo group had a higher 60-day all-cause mortality compared to the 5-FU/LV/bevacizumab group (13.5% vs. 5.0%). Death due to disease progression in the first 60 days was similar (5.8% vs. 4.0%) in the two groups. In the 5-FU/LV/placebo group, deaths within the first 60 days not due to disease progression were attributed to the following: heart failure (1), sepsis (3), diarrhea (2), respiratory failure (1), and pulmonary embolus (1). In the 5-FU/LV/bevacizumab group, the single early death not due to disease progression was attributed to a myocardial infarction.

The results of this clinical trial further demonstrate that bevacizumab, a humanized monoclonal antibody against VEGF, provides important clinical benefit when added to first-line chemotherapy for the treatment of metastatic colorectal cancer. When compared with 5-FU/LV alone, the addition of bevacizumab prolonged median survival by 3.7 months, progression-free survival by 3.7 months, and response duration by 2.4 months, and increased the response rate by 11%.

These results should be viewed in the context of the study population. Specifically selected were patients who were poor candidates for first-line irinotecan-containing therapy, either because of a low likelihood of benefit or a high likelihood of treatment-associated toxicities. A careful analysis of the pivotal irinotecan trials showed that clinical benefit from this agent was confined to patients with a normal ECOG performance status (PS=0).21, 22 Advanced age, prior pelvic radiation therapy, impaired performance status, and low serum albumin have all been reported to increase irinotecan-associated toxicities. 23-27 Patients with these characteristics are in need of alternative therapeutic options. A retrospective subset analysis from a smaller randomized phase II trial was previously conducted evaluating bevacizumab and 5-FU/LV in CRC and noted bevacizumab provided a substantial treatment effect in the subset of patients with baseline PS 1 or 2 (median survival, 6.3 months vs. 15.2 months), in the subset aged ≧65 years (11.2 months vs. 17.7 months), and in the subset with serum albumin <3.5 (8.1 months versus 14.1 months). These results encouraged us to design the current trial, specifically including a poor-prognosis study population and powering the trial to detect a large treatment effect on survival. We were largely successful in enrolling a population different from that in the concurrently conducted pivotal trial of IFL/placebo versus IFL/bevacizumab. Compared with the pivotal trial, patients in the present trial had a higher median age (72 vs. 61 years) and substantially more patients had a performance status >0 (72% vs. 43%) and albumin ≦3.5 mg/dL (46% vs. 33%).

Despite this high-risk study population, the regimen of 5-FU/LV/bevacizumab appeared to be well tolerated. The well-described bevacizumab-associated adverse event of grade 3 hypertension was seen in 16% of the 5-FU/LV/bevacizumab group versus 3% in the 5-FU/LV/placebo group. No cases of grade 4 hypertension occurred. Proteinuria of any grade was seen in 38% of the 5-FU/LV/bevacizumab group versus 19% of the 5-FU/LV/placeb group; however, only a single patient in the bevacizumab group developed grade 3 proteinuria, and there were no cases of grade 4 proteinuria. No increases in grade 3 or 4 bleeding or venous thrombotic events were seen in bevacizumab-treated patients. There was an imbalance in the incidence of arterial thrombotic events: 10% in the 5-FU/LV/bevacizumab group compared with 4.8% in the 5-FU-/LV placebo group. A similar imbalance was noted in the pivotal bevacizumab trial (1.0% in the IFL/placebo group and 3.3% in the IFL/bevacizumab group). The more advanced age of the population included in the present study may have contributed to a higher overall incidence of this adverse event, however the imbalance in both studies is noteworthy. Large, observational safety trials may be required to further define the incidence and potential risk factors for these, and other, uncommon adverse events associated with bevacizumab therapy.

In summary, these data demonstrate that bevacizumab, when combined with bolus 5-FU/LV, provides substantial clinical benefit for patients with previously untreated metastatic colorectal cancer who are deemed to be poor candidates for irinotecan-containing therapy. Together with the pivotal trial results, these data strengthen the evidence that bevacizumab-based, 5-FU/LV-containing therapy should be considered a standard option for the initial treatment of metastatic colorectal cancer.

What is claimed is:

1. A method for treating cancer in a patient comprising administering an effective amount of bevacizumab and assessing the patient for gastrointestinal perforation during treatment with bevacizumab.

2. The method of claim 1, wherein the cancer is colorectal cancer, rectal cancer, breast cancer, non-small cell lung cancer, renal cancer, prostate cancer, non-Hodgkin's lymphoma, liver cancer, pancreatic cancer, soft-tissue sarcoma, Kaposi's sarcoma, carcinoid carcinoma, head and neck cancer, melanoma, ovarian cancer, mesothelioma, multiple myeloma or glioblastoma.

3. The method of claim 1, wherein the method further comprises administering a chemotherapeutic agent.

4. The method of claim 3, wherein the chemotherapeutic agent is selected from the group consisting of alkylating agents, antimetabolites, folio acid analogs, pyrimidine analogs, purine analogs, vinca alkaloids, epipodophyllotoxins, antibiotics, L-Asparaginase, topoisomerase inhibitor, interferons, platinum coordination complexes, anthracenedione substituted urea, methyl hydrazine derivatives, adrenocortical suppressant, adrenocorticosteroids, progestins, estrogens, antiestrogen, androgens, antiandrogen, and gonadotropin-releasing hormone analog.

5. The method of claim 1, wherein the bevacizumab is administered to the patient at about 5-15 mg/kg every 2-3 weeks.

* * * * *